(12) United States Patent
Bate et al.

(10) Patent No.: US 8,779,239 B2
(45) Date of Patent: Jul. 15, 2014

(54) YIELD ENHANCEMENT IN PLANTS BY MODULATION OF AP2 TRANSCRIPTION FACTOR

(75) Inventors: Nicholas J Bate, Urbandale, IA (US); Jennifer Youjin Chung, Johnston, IA (US); Jeffrey E Habben, Urbandale, IA (US)

(73) Assignee: Pioneeri Hi-Bred International, Inc., Johnston, IA (US)

( * ) Notice: Subject to any disclaimer, the term of this patent is extended or adjusted under 35 U.S.C. 154(b) by 469 days.

(21) Appl. No.: 12/773,070

(22) Filed: May 4, 2010

(65) Prior Publication Data

US 2010/0281578 A1 Nov. 4, 2010

Related U.S. Application Data

(60) Provisional application No. 61/175,087, filed on May 4, 2009.

(51) Int. Cl.
*A01H 5/00* (2006.01)
*C12N 15/29* (2006.01)
*C12N 15/82* (2006.01)

(52) U.S. Cl.
USPC .......................... 800/298; 800/290; 800/320

(58) Field of Classification Search
None
See application file for complete search history.

(56) References Cited

U.S. PATENT DOCUMENTS

2004/0019927 A1   1/2004   Sherman et al.
2007/0022495 A1   1/2007   Reuber et al.

FOREIGN PATENT DOCUMENTS

WO   WO02/13227 A2 *   2/2003

OTHER PUBLICATIONS

Lazar et al. (Mol Cell Biol 8(3):1247-52 (1988).*
Zhao, et al.; "OsAP2-1, an AP2-like gene from *Oryza sativa*, is required for flower development and male fertility"; Sexual Plant Reproduction (2006) 19(4):197-206.
Kim, et al.; "Phylogeny and Domain Evolution in the APETALA2-like Gene Family"; Molecular Biology and Evolution (2006) 23(1):107-120.
UniProt Database Accession Number: Q9FH54; Apr. 14, 2009.
Seok, et al.; "Investigation of AP2/ERF Genes Involved in Abiotic Stress Signal Transduction in *Arabidopsis* and Rice".

* cited by examiner

*Primary Examiner* — David H Kruse
*Assistant Examiner* — Russell Boggs
(74) *Attorney, Agent, or Firm* — Pioneer Hi-Bred Int'l Inc.

(57) ABSTRACT

Compositions and methods for modulating flower organ development, leaf formation, phototropism, apical dominance, fruit development, initiation of roots and for increasing yield in a plant are provided. The compositions include an AP2 transcription factor sequence. Compositions of the invention comprise amino acid sequences and nucleotide sequences selected from SEQ ID NOS: 1-11 as well as variants and fragments thereof. Nucleotide sequences encoding the AP2 transcription factors are provided in DNA constructs for expression in a plant of interest are provided for modulating the level of an AP2 transcription factor sequence in a plant or a plant part are provided. The methods comprise introducing into a plant or plant part a heterologous polynucleotide comprising an AP2 transcription factor sequence of the invention. The level of the AP2 transcription factor polypeptide can be increased or decreased. Such method can be used to increase the yield in plants; in one embodiment, the method is used to increase grain yield in cereals.

19 Claims, 8 Drawing Sheets

```
                        1                                                 50
SEQ ID NO: 2      (1)   MYGKRPFGGDESEEREEDENLFPVFSARSQHDMRVMVSALTQVIGNQQSK
SEQ ID NO:13      (1)   ----------------------------------MVSALSRVIEN----
SEQ ID NO:12      (1)   --------------MVTALAHVIRAAPDLHLPHHPSSSASAAAHPQQAS
SEQ ID NO:14      (1)   -----------------------------------MEASNNESAPT---
SEQ ID NO:15      (1)   ----------------------MDPLASQHQHNHLEDNNQTLTHN----
Consensus         (1)                               I    H     MSASV N 51                                               100
SEQ ID NO: 2     (51)   SHDNISSIDDNYPSVYNPQDPNQQVAPTHQDQGDLRRRHYRGVRQRPWGK
SEQ ID NO:13     (12)   ---------PTDPPVKQELDKSDQHQPDQDQP---RRRHYRGVRQRPWGK
SEQ ID NO:12     (36)   S-------FYPTAAAAASSPSDQLAAAAAAAEEQGRRRHYRGVRQRPWGK
SEQ ID NO:14     (12)   ---------AEAAAGSGPAGGEGRKGKAPKGGPENGKFRYRGVRQRSWGK
SEQ ID NO:15     (24)   --------NPQSDSTTDSSTSSAQRKRKGKGGPDNSKFRYRGVRQRSWGK
Consensus        (51)                A    S     Q A    G D RRRHYRGVRQRPWGK 101                                              150
SEQ ID NO: 2    (101)   WAAEIRDPKKAARVWLGTFETAESAALAYDEAALKFKGSKAKLNFP----
SEQ ID NO:13     (50)   WAAEIRDPKKAARVWLGTFETAEEAALAYDRAALKFKGTKAKLNFP----
SEQ ID NO:12     (79)   WAAEIRDPKKAARVWLGTFDTAEDAAIAYDEAALRFKGTKAKLNFPERVQ
SEQ ID NO:14     (53)   WVAEIREPRKRSRKWLGTFATAEDAARAYDRAALLLYGPRAHLNLTSPPP
SEQ ID NO:15     (66)   WVAEIREPRKRTRKWLGTFATAEDAARAYDRAAVYLYGSRAQLNLTPSSP
Consensus       (101)   WAAEIRDPKKAARVWLGTFETAEDAALAYDRAALKFKGSKAKLNFP 151                                              200
SEQ ID NO: 2    (147)   ERVQLGSNSTYYS-----S-NQIPQMEPQSIPNYNQYYHDASSGDMLSFN
SEQ ID NO:13     (96)   ERVQGPTTTTTISHAPRGVSESMNSPPPRPGPPSTTTTSWPMTYNQDILQ
SEQ ID NO:12    (129)   GRTDLGFLVTRGI-PPAATHGGGYYPSSSPAAGACPPPRQQQTVVPYPDL
SEQ ID NO:14    (103)   PTLAAPRSHPHSS-ATSSAPPALRPLLPRPPLHQLSSDGAPAPDFHYHNQ
SEQ ID NO:15    (116)   SSVSSSSSSSVSAASSPSTSSSSTQTLRPLLPRPAAATVGGGANFGPYGIP
Consensus       (151)     RV     SSST S APS S  SI  L P P   A T     AT  Y Q 201                                              250
SEQ ID NO: 2    (191)   LGGGYGSGTGYSMSHDNSTTTAATTSS-SSGGSSRQQEEQDYARFWRFGD
SEQ ID NO:13    (146)   YAQLLTSNNEVDLSYYTSTLFSQPFSTPSSSSSSSQQTQQQQLQQQQQQR
SEQ ID NO:12    (178)   MRYAQLLQGGVGGSYMPFGGAATMSSSTVSSSSAPQILDFSTQQLIRAGP
SEQ ID NO:14    (152)   FQRRLLPQPTPTLYYANTATASTVTTSVPTRVAVPQEPAIAPAVGSSTSL
SEQ ID NO:15    (166)   FNNNIFLNGGTSMLCPSYGFFPQQQQQQNQMVQMGQFQHQQYQNLHSNTN
Consensus       (201)   F   L  N G SLSY  SG A   TSS S  SS Q     Q   Q 251                                              300
SEQ ID NO: 2    (240)   S------------------------SSSPHSGY----------------
SEQ ID NO:13    (196)   E------------------------EEEKNYGYNYYNPRE---------
SEQ ID NO:12    (228)   P--------------------SPMPSSGSGSATAAASSTTSASSPGAW
SEQ ID NO:14    (202)   Q------EP-----------QVGTPEEARGEAGWDYNGGEEEDYAAALL
SEQ ID NO:15    (216)   NNKISDIELTDVPVTNSTSFHHEVALGQEQGGSGCNNNSSMEDLNSLAGS
Consensus       (251)                                S  SGY       E  S A 301                                              350
SEQ ID NO: 2    (249)   -------------------------------------------------
SEQ ID NO:13    (213)   -------------------------------------------------
SEQ ID NO:12    (256)   PYGGSERKKKDSSS-----------------------------------
SEQ ID NO:14    (234)   WDEPEPFFWFDVFLK----------------------------------
SEQ ID NO:15    (266)   VGSSLSITHPPPLVDPVCSMGLDPGYMVGDGSSTIWPFGGEEEYSHNWGS
Consensus       (301)

351        363
SEQ ID NO: 2    (249)   -------------
SEQ ID NO:13    (213)   -------------
SEQ ID NO:12    (270)   -------------
SEQ ID NO:14    (249)   -------------
SEQ ID NO:15    (316)   IWDFIDPILGEFY
Consensus       (351)
```

FIGURE 1

```
SEQ NO: 2    AT-AP2 133992   (1)  MYGKRPFGGDESEREEDENLFPVFSARSQHDMRVMVSALTQVIGNQQSK
SEQ ID NO: 4 GM-AP2-2        (1)  ------------------------------------------MSTNQNT
             Consensus       (1)                                              Q
                                  51                                                100

AT-AP2 133992 NP_200995     (51)  SHDNISSIDDNYPSVYNPQDPNQQVAPTHQDQGDLRRHYRGVRQRPWGK
              GM-AP2-2       (8)  TFFPLPHGQITTSEFVNSQN--NPSQATNQGIDDIRKKHYRGVRQRPWGK
              Consensus     (51)                    N Q          T Q    D R  HYRGVRQRPWGK
                                  101                                               150

AT-AP2 133992 NP_200995    (101)  WAAEIRDPKKAARVWLGTFETAESAALAYDEAALKFKGSKAKLNFPERVQ
              GM-AP2-2      (56)  WAAEIRDPKKAARVWLGTFDTAEAAAMAYDAAALRFKGNKAKLNFPERVV
              Consensus    (101)  WAAEIRDPKKAARVWLGTF  TAE AA  AYD AAL FKG KAKLNFPERV
                                  151                                               200

AT-AP2 133992 NP_200995    (151)  LGS---NSTYYSSNQIPQMEPQSIPNYNQYYHDASSGDMLSFNLGGGYGS
              GM-AP2-2     (106)  MPIPSQTNTNTNMNNTTSSSSAPTTQPSSLPPPPSQSLQNSSNNNSSLSS
              Consensus    (151)               T Y N                     S    S N      S
                                  201                                               250

AT-AP2 133992 NP_200995    (198)  GTGYSMSHDNSTTTAATTSSSSGGSSRQQEEQDYARFWRFGDSSSSPHSG
              GM-AP2-2     (156)  -EGFPNLEEYARLLNCSDDDDFQRVALGLYQHHNNEDYIYGSSQPPPVPF
              Consensus    (201)   G                                         G S    P
                                  251                284

AT-AP2 133992 NP_200995    (248)  Y-------------------------------------
              GM-AP2-2     (205)  FVSSYSSSSAMASSFSDFLGQGGSGFDEENKRGS
              Consensus    (251)
```

YIELD ENHANCEMENT IN PLANTS BY MODULATION OF AP2 TRANSCRIPTION FACTOR

CROSS-REFERENCE

This utility application claims the benefit of U.S. Provisional Application Ser. No. 61/175,087, filed May 4, 2009, which is incorporated herein by reference.

FIELD OF THE INVENTION

The present invention is drawn to the field of genetics and molecular biology. More particularly, the compositions and methods are directed to modulation of transcription and improving yield in plants.

BACKGROUND OF THE INVENTION

Grain yield improvements by conventional breeding have nearly reached a plateau in crop plants. It is natural then to explore some alternative, non-conventional approaches that could be employed to obtain further yield increases.

Technologic developments continually advance in an effort to address the need to increase plant yield in order to feed the expanding world population. Biotechnology is playing an increasingly important role in this effort by providing, for example, plants having increased resistance to drought and insect infestation. For many plants such as corn, rice and soybean, seed provides the source of food products, including grain and can be eaten directly or processed into flour, milk products and the like. For other plants, edible seeds, roots, stems, leaves, bulbs and tubers provide a source of vegetables. Fruits, which are the ripened reproductive body of plants, also are an important food source.

Because many foods are derived, either directly or indirectly, as a result of plant flowering, methods for increasing flowering efficiency and numbers of flowers produced of plants can result in increased yield. Further, while providing a means to increase yield of crop plants, such tools also can be useful in the ornamental plant industry, providing, for example, a means to increase the number and/or size of flowers produced by a plant.

Nearly all crops may be benefited by the manipulation of growth and development characteristics. As such, mutations in the reception and signal transduction of gibberellins leading to dwarf-like plants have been described as advantageous in many crop plants (U.S. Pat. No. 6,307,126; U.S. Pat. No. 6,762,348; U.S. Pat. No. 6,830,930; U.S. Pat. No. 6,794,560). This was especially true in high-yielding, semi-dwarf wheat varieties where the reduced plant stature was most advantageous in increasing grain production per plant and superior straw strength. The shorter, stronger straw greatly reduces the losses resulting from lodging or flattening of the standing wheat plants by rain and high winds. In addition a concomitant increase in harvest index was evident shifting more photoassimilates from vegetative growth components to the grain.

Methods and compositions are needed in the art which can employ such sequences to modulate harvest index and yield in plants.

BRIEF SUMMARY OF THE INVENTION

Compositions and methods of the invention comprise and employ AP2 transcription factor polypeptides and polynucleotides that are involved in modulating plant development, morphology, and physiology.

The compositions include AP2 transcription factor sequences from *Arabidopsis* and soybean (*Glycine max*). Compositions of the invention comprise amino acid sequences and nucleotide sequences selected from SEQ ID NOS: 1-5 as well as variants and fragments thereof.

Nucleotide sequences encoding the AP2 transcription factor are provided in DNA constructs for expression in a plant of interest. Expression cassettes, plants, plant cells, plant parts, and seeds comprising the sequences of the invention are further provided. In specific embodiments, the polynucleotide is operably linked to a constitutive promoter.

Methods for modulating the level of an AP2 transcription factor sequence in a plant or a plant part are provided. The methods comprise introducing into a plant or plant part a heterologous polynucleotide comprising an AP2 transcription factor sequence, an AP2 DNA binding domain, or an AP2 TRANSCRIPTION activation domain of the invention. The level of the AP2 transcription factor polypeptide can be increased or decreased. Such method can be used to increase the yield in plants; in one embodiment, the method is used to increase grain yield in crop plants.

BRIEF DESCRIPTION OF THE FIGURES

FIG. 1 provides an alignment of several AP2 transcription factor sequences from *Zea mays, Arabidopsis thaliana, Oryza sativum,* and *Antirrhinum majus*. The AP2 transcription factor consensus domain (SEQ ID NO: 5) is single-underlined and the polyserine (SEQ ID NO:2 amino acid positions 226-233 and 240-246) and polyglycine consensus domains (SEQ ID NO: 2 amino acid positions 192-210) are double underlined.

FIG. 2. Alignment of the *Arabidopsis* AP2 and soybean AP2 sequence.

DETAILED DESCRIPTION OF THE INVENTION

Figure 3:
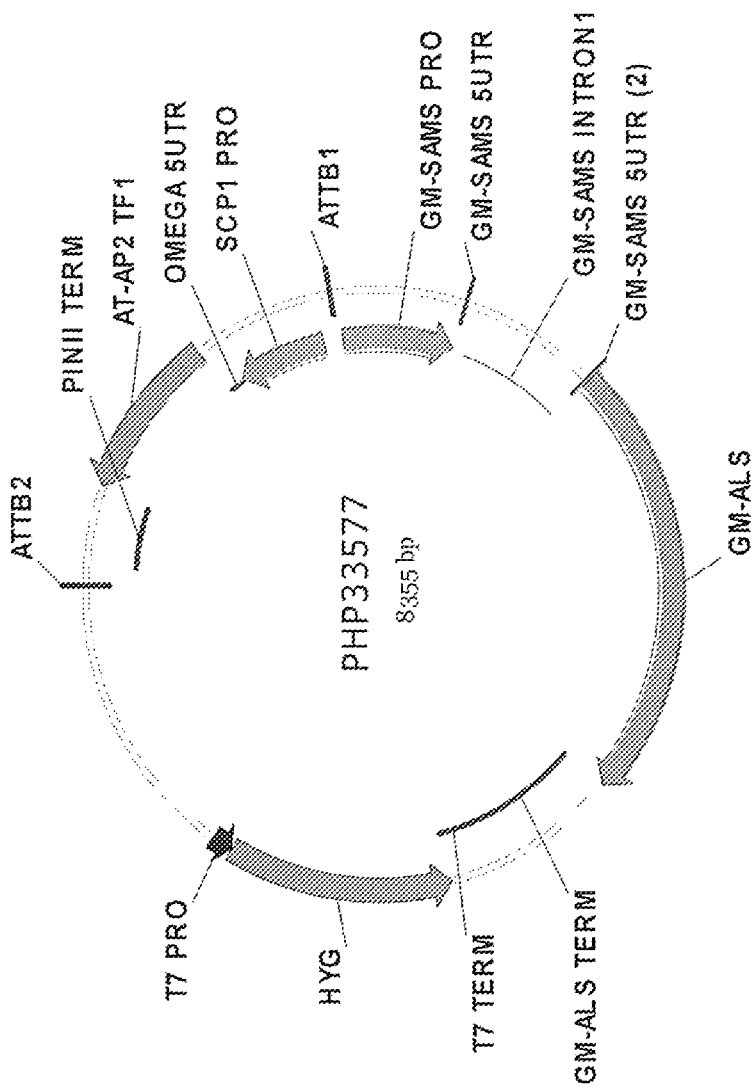
FIG. 3. Plant transformation vector expressing the *Arabidopsis* AP2 gene (AT-AP2 TF1) under the control of the constitutive SCP1 promoter.
Figure 4:
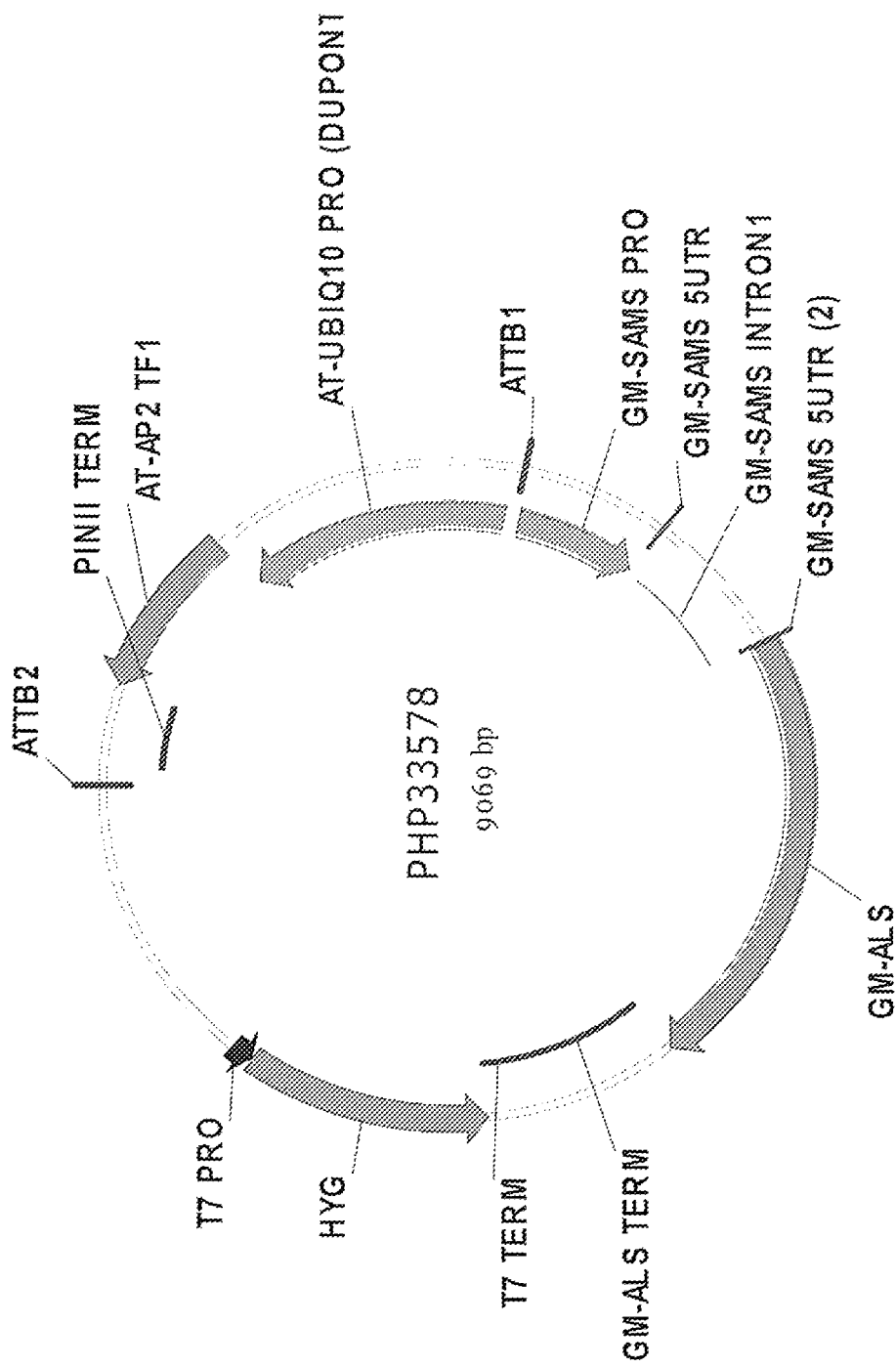
FIG. 4. Plant transformation vector expressing the *Arabidopsis* AP2 gene (AT-AP2 TF1) under the control of the constitutive AT-UBQ10 promoter.
Figure 5:
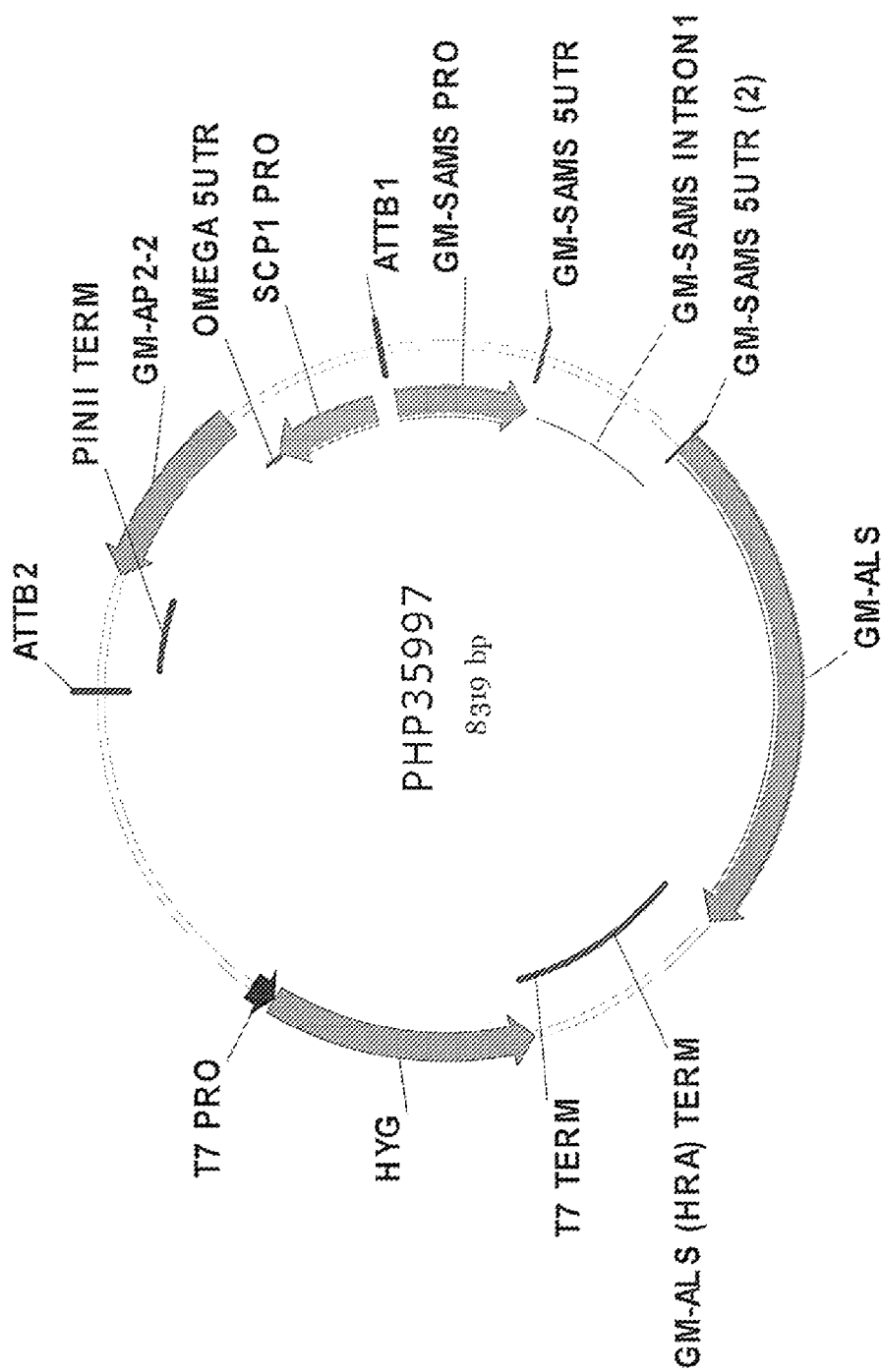
FIG. 5. Plant transformation vector expressing the Soybean AP2 gene (GM-AP2-2) under the control of the constitutive SCP1 promoter.
Figure 6:
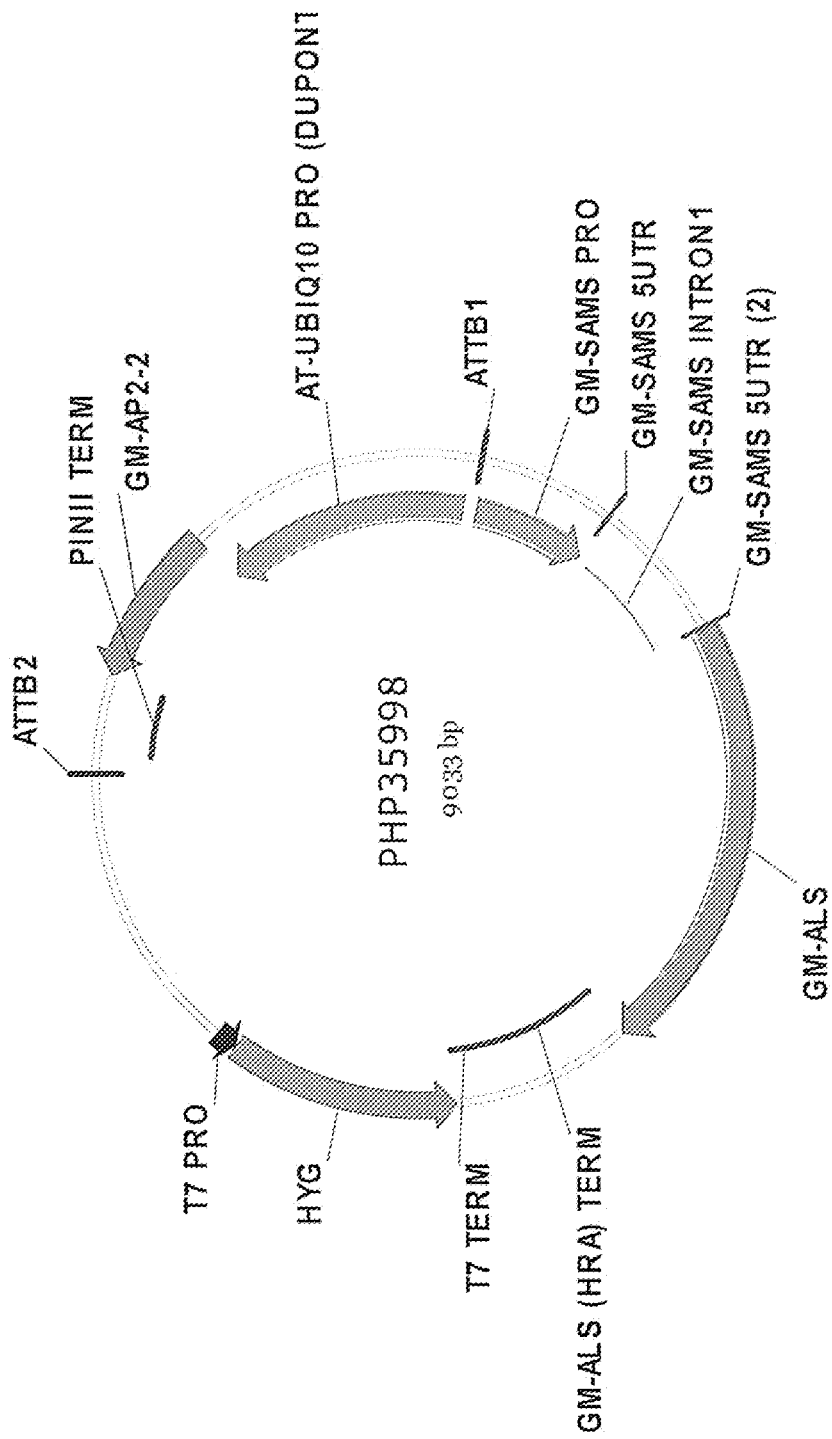
FIG. 6. Plant transformation vector expressing the Soybean AP2 gene (GM-AP2-2) under the control of the constitutive AT-UBQ10 promoter.

The present inventions now will be described more fully hereinafter with reference to the accompanying drawings, in which some, but not all embodiments of the inventions are shown. Indeed, these inventions may be embodied in many different forms and should not be construed as limited to the embodiments set forth herein; rather, these embodiments are provided so that this disclosure will satisfy applicable legal requirements.

Many modifications and other embodiments of the inventions set forth herein will come to mind to one skilled in the art to which these inventions pertain having the benefit of the teachings presented in the foregoing descriptions and the associated drawings. Therefore, it is to be understood that the inventions are not to be limited to the specific embodiments disclosed and that modifications and other embodiments are intended to be included within the scope of the appended claims. Although specific terms are employed herein, they are used in a generic and descriptive sense only and not for purposes of limitation.

I. Overview

Methods and compositions are provided to promote floral organ development, root initiation, and yield, and for modulating leaf formation, phototropism, apical dominance, fruit development and the like, in plants. The compositions and methods of the invention result in improved plant or crop yield by modulating in a plant the level of at least one AP2 transcription factor polypeptide or a polypeptide having a biologically active variant or fragment of an AP2 transcription factor polypeptide of the invention.

II. Compositions

Compositions of the invention include AP2 transcription factor polynucleotides and polypeptides and variants and fragments thereof that are involved in regulating transcription. AP2 transcription factor encodes a plant protein with an AP2 domain. In addition, a nuclear localization signal for transport to the nucleus as well as polyserine and polyglycine domains are present in the AP2 protein. By "corresponding to" is intended that the recited amino acid positions for each domain relate to the amino acid positions of the recited SEQ ID NO, and that polypeptides comprising these domains may be found by aligning the polypeptides with the recited SEQ ID NO: using standard alignment methods.

The AP2 transcription factor sequences of the invention act as activators or repressors of transcription of effector genes or regulators. While not bound by any theory of mechanism, AP2 transcription factor may control aspects of plant development important for the establishment of yield forming structures such as flowers or flower branches.

AP2 transcription factor is expressed at very low levels and is undetectable by MPSS profiling. Low levels of AP2 expression suggest it encodes a tightly regulated control factor and that ectopic expression of AP2 results in a plant with altered plant morphology that may positively impact plant yield.

As used herein, a "AP2 transcription factor" or "AP2 transcription factor" sequence comprises a polynucleotide encoding or a polypeptide having the the AP2 transcription factor domain or a biologically active variant or fragment of the AP2 transcription factor domain. See, for example, Jurata and Gill, (1997) *Mol. Cell. Biol.* 17:5688-98 and Franks, et al., (2002) *Development* 129:253-63.

In one embodiment, the present invention provides isolated AP2 transcription factor polypeptides comprising amino acid sequences as shown in SEQ ID NOS: 2 and 4 and fragments and variants thereof. Further provided are polynucleotides comprising the nucleotide sequence set forth in SEQ ID NO: 1 and sequences comprising a polynucleotide encoding an AP2 domain (SEQ ID NO: 5).

The invention encompasses isolated or substantially purified polynucleotide or protein compositions. An "isolated" or "purified" polynucleotide or protein, or biologically active portion thereof, is substantially or essentially free from components that normally accompany or interact with the polynucleotide or protein as found in its naturally occurring environment. Thus, an isolated or purified polynucleotide or protein is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb or 0.1 kb of nucleotide sequence that naturally flank the polynucleotide in genomic DNA of the cell from which the polynucleotide is derived. A protein that is substantially free of cellular material includes preparations of protein having less than about 30%, 20%, 10%, 5% or 1% (by dry weight) of contaminating protein. When the protein of the invention or biologically active portion thereof is recombinantly produced, optimally culture medium represents less than about 30%, 20%, 10%, 5% or 1% (by dry weight) of chemical precursors or non-protein-of-interest chemicals.

Fragments and variants of the AP2 transcription factor domain or AP2 transcription factor polynucleotides and proteins encoded thereby are also encompassed by the methods and compositions of the present invention. By "fragment" is intended a portion of the polynucleotide or a portion of the amino acid sequence. Fragments of a polynucleotide may encode protein fragments that retain the biological activity of the native protein and hence regulate transcription. For example, polypeptide fragments will comprise the AP2 transcription factor domain (SEQ ID NO: 5) or the polyserine (SEQ ID NOS: 7-11) or polyglycine domain (SEQ ID NO: 6). In some embodiments, the polypeptide fragment will comprise both the AP2 transcription factor domain and the polyserine or polyglutamine domain. Alternatively, fragments that are used for suppressing or silencing (i.e., decreasing the level of expression) of an AP2 transcription factor sequence need not encode a protein fragment, but will retain the ability to suppress expression of the target sequence. In addition, fragments that are useful as hybridization probes generally do not encode fragment proteins retaining biological activity. Thus, fragments of a nucleotide sequence may range from at least about 18 nucleotides, about 20 nucleotides, about 50 nucleotides, about 100 nucleotides and up to the full-length polynucleotide encoding the proteins of the invention.

A fragment of a polynucleotide encoding an AP2 transcription factor domain or an AP2 transcription factor polypeptide will encode at least 15, 25, 30, 50, 100, 150, 200, 250, 300, 350, 400, 450, 500, 550, 600, 650, 675, 700, 725, 750, 775, 800, 825 contiguous amino acids, or up to the total number of amino acids present in a full-length AP2 transcription factor domain or AP2 transcription factor protein (i.e., SEQ ID NO: 2). Fragments of an AP2 transcription factor domain or an AP2 transcription factor polynucleotide that are useful as hybridization probes, PCR primers or as suppression constructs generally need not encode a biologically active portion of an AP2 transcription factor protein or an AP2 transcription factor domain.

A biologically active portion of a polypeptide comprising an AP2 transcription factor domain, or an AP2 transcription factor protein can be prepared by isolating a portion of an AP2 transcription factor polynucleotide, expressing the encoded portion of the AP2 transcription factor protein (e.g., by recombinant expression in vitro) and assessing the activity of the encoded portion of the AP2 transcription factor protein. Polynucleotides that are fragments of an AP2 transcription factor nucleotide sequence or a polynucleotide sequence comprising an AP2 transcription factor domain comprise at least 16, 20, 50, 75, 100, 150, 200, 250, 300, 350, 400, 450, 500, 550, 600, 650, 700, 800, 900, 1,000, 1,100, 1,200, 1,300, 1,400, 1,500, 1,600, 1,700, 1,800, 1,900, 2,000, 2,050, 2,100, 2,150, 2,200, 2,250, 2,300, 2,350, 2,400, 2,450, 2,500 contiguous nucleotides or up to the number of nucleotides present in a full-length AP2 transcription factor domain or in an AP2 transcription factor polynucleotide (i.e., SEQ ID NOS: 1 and 3, 919 and 1217 nucleotides, respectively).

"Variants" is intended to mean substantially similar sequences. For polynucleotides, a variant comprises a deletion and/or addition of one or more nucleotides at one or more internal sites within the native polynucleotide and/or a substitution of one or more nucleotides at one or more sites in the native polynucleotide. As used herein, a "native" polynucleotide or polypeptide comprises a naturally occurring nucleotide sequence or amino acid sequence, respectively. For polynucleotides, conservative variants include those sequences that, because of the degeneracy of the genetic code, encode the amino acid sequence of one of the AP2 transcription factor polypeptides or of an AP2 transcription factor domain. Naturally occurring allelic variants such as these can be identified with the use of well-known molecular biology techniques, as, for example, with polymerase chain reaction (PCR) and hybridization techniques as outlined below. Variant polynucleotides also include synthetically derived polynucleotide, such as those generated, for example, by using site-directed mutagenesis but which still encode a polypeptide comprising an AP2 transcription factor domain (or both) or an AP2 transcription factor polypeptide that is capable of regulating transcription or that is capable of reducing the level of expression (i.e., suppressing or silencing) of an AP2 transcription factor polynucleotide. Generally, variants of a particular polynucleotide of the invention will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to that particular polynucleotide as determined by sequence alignment programs and parameters described elsewhere herein.

Variants of a particular polynucleotide of the invention (i.e., the reference polynucleotide) can also be evaluated by comparison of the percent sequence identity between the polypeptide encoded by a variant polynucleotide and the polypeptide encoded by the reference polynucleotide. Thus, for example, an isolated polynucleotide that encodes a polypeptide with a given percent sequence identity to the polypeptide of SEQ ID NO. 2 or SEQ ID NO: 4 are disclosed. Percent sequence identity between any two polypeptides can be calculated using sequence alignment programs and parameters described elsewhere herein. Where any given pair of polynucleotides of the invention is evaluated by comparison of the percent sequence identity shared by the two polypeptides they encode, the percent sequence identity between the two encoded polypeptides is at least about 40%, 45%, 50%, 55%, 60%, 65%, 70%, 75%, 80%, 85%, 90%, 91%, 92%, 93%, 94%, 95%, 96%, 97%, 98%, 99% or more sequence identity.

"Variant" protein is intended to mean a protein derived from the native protein by deletion or addition of one or more amino acids at one or more internal sites in the native protein and/or substitution of one or more amino acids at one or more sites in the native protein. Variant proteins encompassed by the present invention are biologically active, that is they continue to possess the desired biological activity of the native protein, that is, regulate transcription as described herein. Such variants may result from, for example, genetic polymorphism or from human manipulation. Biologically active variants of an AP2 transcription factor protein of the invention of an AP2 transcription factor domain will have at least about 40%, 45%, 50%, 55%, 60%, 65%, 70%, 75%, 80%, 85%, 90%, 91%, 92%, 93%, 94%, 95%, 96%, 97%, 98%, 99% or more sequence identity to the amino acid sequence for the AP2 transcription factor protein or the consensus AP2 transcription factor domain as determined by sequence alignment programs and parameters described elsewhere herein. A biologically active variant of an AP2 transcription factor protein of the invention or of an AP2 transcription factor domain may differ from that protein by as few as 1-15 amino acid residues, as few as 1-10, such as 6-10, as few as 5, as few as 4, 3, 2 or even 1 amino acid residue.

The polynucleotides of the invention may be altered in various ways including amino acid substitutions, deletions, truncations and insertions. Methods for such manipulations are generally known in the art. For example, amino acid sequence variants and fragments of the AP2 transcription factor proteins or AP2 transcription factor domains can be prepared by mutations in the DNA. Methods for mutagenesis and polynucleotide alterations are well known in the art. See, for example, Kunkel (1985) *Proc. Natl. Acad. Sci. USA* 82:488-492; Kunkel, et al., (1987) *Methods in Enzymol.* 154: 367-382; U.S. Pat. No. 4,873,192; Walker and Gaastra, eds. (1983) *Techniques in Molecular Biology* (MacMillan Publishing Company, New York) and the references cited therein. Guidance as to appropriate amino acid substitutions that do not affect biological activity of the protein of interest may be found in the model of Dayhoff, et al., (1978) *Atlas of Protein Sequence and Structure* (Natl. Biomed. Res. Found., Washington, D.C.), herein incorporated by reference. Conservative substitutions, such as exchanging one amino acid with another having similar properties, may be optimal.

Thus, the genes and polynucleotides of the invention include both the naturally occurring sequences as well as mutant forms. Likewise, the proteins of the invention encompass both naturally occurring proteins as well as variations and modified forms thereof. Such variants will continue to possess the desired activity (i.e., the ability to regulate transcription or decrease the level of expression of a target AP2 transcription factor sequence). In specific embodiments, the mutations that will be made in the DNA encoding the variant do not place the sequence out of reading frame and do not create complementary regions that could produce secondary mRNA structure. See, EP Patent Application Publication Number 75,444.

The deletions, insertions and substitutions of the protein sequences encompassed herein are not expected to produce radical changes in the characteristics of the protein. However, when it is difficult to predict the exact effect of the substitution, deletion or insertion in advance of doing so, one skilled in the art will appreciate that the effect will be evaluated by routine screening assays. For example, the activity of an AP2 transcription factor polypeptide can be evaluated by assaying for the ability of the polypeptide to regulate transcription. Various methods can be used to assay for this activity, including, directly monitoring the level of expression of a target gene at the nucleotide or polypeptide level. Methods for such an analysis are known and include, for example, Northern blots, S1 protection assays, Western blots, enzymatic or colorimetric assays. In specific embodiments, determining if a sequence has AP2 transcription factor activity can be assayed by monitoring for an increase or decrease in the level or activity of target genes, including AG. For example, in specific embodiments, an AP2 transcription factor sequence can modulate transcription of target genes such as the floral homeotic gene AG, genes involved in auxin-regulated growth and development, and the like. See, Sridhar, et al., (2004) *Proc. Natl. Acad. Sci. USA* 101:11494-11499, herein incorporated by reference. Alternatively, methods to assay for a modulation of transcriptional activity can include monitoring for an alteration in the phenotype of the plant. For example, as discussed in further detail elsewhere herein, modulating the level of an AP2 transcription factor polypeptide can result in abnormal flower formation, root initiation and alteration of yield. Methods to assay for these changes are discussed in further detail elsewhere herein.

Variant polynucleotides and proteins also encompass sequences and proteins derived from a mutagenic and recombinogenic procedure such as DNA shuffling. With such a procedure, one or more different AP2 transcription factor coding sequences can be manipulated to create a new AP2 transcription factor sequence or AP2 transcription factor domain possessing the desired properties. In this manner, libraries of recombinant polynucleotides are generated from a population of related sequence polynucleotides comprising sequence regions that have substantial sequence identity and can be homologously recombined in vitro or in vivo. For example, using this approach, sequence motifs encoding a domain of interest may be shuffled between the AP2 transcription factor gene of the invention and other known AP2 transcription factor genes to obtain a new gene coding for a protein with an improved property of interest, such as an increased $K_m$ in the case of an enzyme. Strategies for such DNA shuffling are known in the art. See, for example, Stemmer, (1994) *Proc. Natl. Acad. Sci. USA* 91:10747-10751; Stemmer, (1994) *Nature* 370:389-391; Crameri, et al., (1997) *Nature Biotech.* 15:436-438; Moore, et al., (1997) *J. Mol. Biol.* 272:336-347; Zhang, et al., (1997) *Proc. Natl. Acad. Sci. USA* 94:4504-4509; Crameri, et al., (1998) *Nature* 391:288-291 and U.S. Pat. Nos. 5,605,793 and 5,837,458.

The polynucleotides of the invention can be used to isolate corresponding sequences from other organisms, particularly other plants, more particularly other monocots. In this manner, methods such as PCR, hybridization and the like can be used to identify such sequences based on their sequence homology to the sequences set forth herein. Sequences isolated based on their sequence identity to the entire AP2 transcription factor sequences, or AP2 transcription factor domains of the invention, set forth herein or to variants and fragments thereof are encompassed by the present invention. Such sequences include sequences that are orthologs of the disclosed sequences. "Orthologs" is intended to mean genes derived from a common ancestral gene and which are found in different species as a result of speciation. Genes found in different species are considered orthologs when their nucleotide sequences and/or their encoded protein sequences share at least 60%, 70%, 75%, 80%, 85%, 90%, 91%, 92%, 93%, 94%, 95%, 96%, 97%, 98%, 99% or greater sequence identity. Functions of orthologs are often highly conserved among species. Thus, isolated polynucleotides that can silence or suppress the expression of an AP2 transcription factor sequence or a polynucleotide that encodes for an AP2 transcription factor protein and which hybridize under stringent conditions to the AP2 transcription factor sequences disclosed herein, or to variants or fragments thereof, are encompassed by the present invention.

In a PCR approach, oligonucleotide primers can be designed for use in PCR reactions to amplify corresponding DNA sequences from cDNA or genomic DNA extracted from any plant of interest. Methods for designing PCR primers and PCR cloning are generally known in the art and are disclosed in Sambrook, et al., (1989) *Molecular Cloning: A Laboratory Manual* (2d ed., Cold Spring Harbor Laboratory Press, Plainview, N.Y.). See also, Innis, et al., eds. (1990) *PCR Protocols: A Guide to Methods and Applications* (Academic Press, New York); Innis and Gelfand, eds. (1995) *PCR Strategies* (Academic Press, New York); and Innis and Gelfand, eds. (1999) *PCR Methods Manual* (Academic Press, New York). Known methods of PCR include, but are not limited to, methods using paired primers, nested primers, single specific primers, degenerate primers, gene-specific primers, vector-specific primers, partially-mismatched primers and the like.

In hybridization techniques, all or part of a known polynucleotide is used as a probe that selectively hybridizes to other corresponding polynucleotides present in a population of cloned genomic DNA fragments or cDNA fragments (i.e., genomic or cDNA libraries) from a chosen organism. The hybridization probes may be genomic DNA fragments, cDNA fragments, RNA fragments or other oligonucleotides and may be labeled with a detectable group such as $^{32}P$, or any other detectable marker. Thus, for example, probes for hybridization can be made by labeling synthetic oligonucleotides based on the AP2 transcription factor polynucleotides of the invention. Methods for preparation of probes for hybridization and for construction of cDNA and genomic libraries are generally known in the art and are disclosed in Sambrook, et al., (1989) *Molecular Cloning: A Laboratory Manual* (2d ed., Cold Spring Harbor Laboratory Press, Plainview, N.Y.).

For example, the entire AP2 transcription factor polynucleotide or a polynucleotide encoding an AP2 transcription factor domain disclosed herein or one or more portions thereof, may be used as a probe capable of specifically hybridizing to corresponding AP2 transcription factor polynucleotide and messenger RNAs. To achieve specific hybridization under a variety of conditions, such probes include sequences that are unique among AP2 transcription factor polynucleotide sequences and are optimally at least about 10 nucleotides in length and most optimally at least about 20 nucleotides in length. Such probes may be used to amplify corresponding AP2 transcription factor polynucleotide from a chosen plant by PCR. This technique may be used to isolate additional coding sequences from a desired plant or as a diagnostic assay to determine the presence of coding sequences in a plant. Hybridization techniques include hybridization screening of plated DNA libraries (either plaques or colonies; see, for example, Sambrook, et al., (1989) *Molecular Cloning: A Laboratory Manual* (2d ed., Cold Spring Harbor Laboratory Press, Plainview, N.Y.).

Hybridization of such sequences may be carried out under stringent conditions. By "stringent conditions" or "stringent hybridization conditions" is intended conditions under which a probe will hybridize to its target sequence to a detectably greater degree than to other sequences (e.g., at least 2-fold over background). Stringent conditions are sequence-dependent and will be different in different circumstances. By controlling the stringency of the hybridization and/or washing conditions, target sequences that are 100% complementary to the probe can be identified (homologous probing). Alternatively, stringency conditions can be adjusted to allow some mismatching in sequences so that lower degrees of similarity are detected (heterologous probing). Generally, a probe is less than about 1000 nucleotides in length, optimally less than 500 nucleotides in length.

Typically, stringent conditions will be those in which the salt concentration is less than about 1.5 M Na ion, typically about 0.01 to 1.0 M Na ion concentration (or other salts) at pH 7.0 to 8.3 and the temperature is at least about 30° C. for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° C., and a wash in 1× to 2×SSC (20×SSC=3.0 M NaCl/0.3 M trisodium citrate) at 50 to 55° C. Exemplary moderate stringency conditions include hybridization in 40 to 45% formamide, 1.0 M NaCl, 1% SDS at 37° C. and a wash in 0.5× to 1×SSC at 55 to 60° C. Exemplary high stringency conditions include hybridization in 50% formamide, 1 M NaCl, 1% SDS at 37° C. and a wash in 0.1×SSC at 60 to 65° C. Optionally, wash buffers may comprise about 0.1% to about 1% SDS. Duration of hybridization is generally less than about 24 hours, usually about 4 to about 12 hours. The duration of the wash time will be at least a length of time sufficient to reach equilibrium.

Specificity is typically the function of post-hybridization washes, the critical factors being the ionic strength and temperature of the final wash solution. For DNA-DNA hybrids, the $T_m$ can be approximated from the equation of Meinkoth and Wahl, (1984) *Anal. Biochem.* 138:267-284: $T_m$=81.5° C.+16.6 (log M)+0.41 (% GC)−0.61 (% form) −500/L; where M is the molarity of monovalent cations, % GC is the percentage of guanosine and cytosine nucleotides in the DNA, % form is the percentage of formamide in the hybridization solution, and L is the length of the hybrid in base pairs. The $T_m$ is the temperature (under defined ionic strength and pH) at which 50% of a complementary target sequence hybridizes to a perfectly matched probe. $T_m$ is reduced by about 1° C. for each 1% of mismatching; thus, $T_m$, hybridization, and/or wash conditions can be adjusted to hybridize to sequences of the desired identity. For example, if sequences with ≥90% identity are sought, the $T_m$ can be decreased 10° C. Generally, stringent conditions are selected to be about 5° C. lower than the thermal melting point ($T_m$) for the specific sequence and its complement at a defined ionic strength and pH. However, severely stringent conditions can utilize a hybridization and/or wash at 1, 2, 3 or 4° C. lower than the thermal melting point ($T_m$); moderately stringent conditions can utilize a hybridization and/or wash at 6, 7, 8, 9 or 10° C. lower than the thermal melting point ($T_m$); low stringency conditions can utilize a hybridization and/or wash at 11, 12, 13, 14, 15 or 20° C. lower than the thermal melting point ($T_m$). Using the equation, hybridization and wash compositions, and desired $T_m$, those of ordinary skill will understand that variations in the stringency of hybridization and/or wash solutions are inherently described. If the desired degree of mismatching results in a $T_m$ of less than 45° C. (aqueous solution) or 32° C. (formamide solution), it is optimal to increase the SSC concentration so that a higher temperature can be used. An extensive guide to the hybridization of nucleic acids is found in Tijssen, (1993) *Laboratory Techniques in Biochemistry and Molecular Biology—Hybridization with Nucleic Acid Probes*, Part I, Chapter 2 (Elsevier, New York); and Ausubel, et al., eds. (1995) *Current Protocols in Molecular Biology*, Chapter 2 (Greene Publishing and Wiley-Interscience, New York). See, Sambrook, et al., (1989) *Molecular Cloning: A Laboratory Manual* (2d ed., Cold Spring Harbor Laboratory Press, Plainview, N.Y.).

The following terms are used to describe the sequence relationships between two or more polynucleotides or polypeptides: (a) "reference sequence", (b) "comparison window", (c) "sequence identity" and (d) "percentage of sequence identity."

(a) As used herein, "reference sequence" is a defined sequence used as a basis for sequence comparison. A reference sequence may be a subset or the entirety of a specified sequence; for example, as a segment of a full-length cDNA or gene sequence or the complete cDNA or gene sequence.

(b) As used herein, "comparison window" makes reference to a contiguous and specified segment of a polynucleotide sequence, wherein the polynucleotide sequence in the comparison window may comprise additions or deletions (i.e., gaps) compared to the reference sequence (which does not comprise additions or deletions) for optimal alignment of the two polynucleotides. Generally, the comparison window is at least 20 contiguous nucleotides in length, and optionally can be 30, 40, 50, 100 or longer. Those of skill in the art understand that to avoid a high similarity to a reference sequence due to inclusion of gaps in the polynucleotide sequence a gap penalty is typically introduced and is subtracted from the number of matches.

Methods of alignment of sequences for comparison are well known in the art. Thus, the determination of percent sequence identity between any two sequences can be accomplished using a mathematical algorithm. Non-limiting examples of such mathematical algorithms are the algorithm of Myers and Miller, (1988) *CABIOS* 4:11-17; the local alignment algorithm of Smith, et al., (1981) *Adv. Appl. Math.* 2:482; the global alignment algorithm of Needleman and Wunsch, (1970) *J. Mol. Biol.* 48:443-453; the search-for-local alignment method of Pearson and Lipman, (1988) *Proc. Natl. Acad. Sci.* 85:2444-2448; the algorithm of Karlin and Altschul, (1990) *Proc. Natl. Acad. Sci. USA* 872264, modified as in Karlin and Altschul, (1993) *Proc. Natl. Acad. Sci. USA* 90:5873-5877.

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the GCG Wisconsin Genetics Software Package®, Version 10 (available from Accelrys Inc., 9685 Scranton Road, San Diego, Calif., USA). Alignments using these programs can be performed using the default parameters. The CLUSTAL program is well described by Higgins, et al., (1988) *Gene* 73:237-244 (1988); Higgins, et al., (1989) *CABIOS* 5:151-153; Corpet, et al., (1988) *Nucleic Acids Res.* 16:10881-90; Huang, et al., (1992) *CABIOS* 8:155-65; and Pearson, et al., (1994) *Meth. Mol. Biol.* 24:307-331. The ALIGN program is based on the algorithm of Myers and Miller, (1988) supra. A PAM120 weight residue table, a gap length penalty of 12, and a gap penalty of 4 can be used with the ALIGN program when comparing amino acid sequences. The BLAST programs of Altschul, et al., (1990) *J. Mol. Biol.* 215:403 are based on the algorithm of Karlin and Altschul, (1990) supra. BLAST nucleotide searches can be performed with the BLASTN program, score=100, wordlength=12, to obtain nucleotide sequences homologous to a nucleotide sequence encoding a protein of the invention. BLAST protein searches can be performed with the BLASTX program, score=50, wordlength=3, to obtain amino acid sequences homologous to a protein or polypeptide of the invention. To obtain gapped alignments for comparison purposes, Gapped BLAST (in BLAST 2.0) can be utilized as described in Altschul, et al., (1997) *Nucleic Acids Res.* 25:3389. Alternatively, PSI-BLAST (in BLAST 2.0) can be used to perform an iterated search that detects distant relationships between molecules. See, Altschul, et al., (1997) supra. When utilizing BLAST, Gapped BLAST, PSI-BLAST, the default parameters of the respective programs (e.g., BLASTN for nucleotide sequences, BLASTX for proteins) can be used. See, www.ncbi.nlm.nih.gov. Alignment may also be performed manually by inspection.

Unless otherwise stated, sequence identity/similarity values provided herein refer to the value obtained using GAP Version 10 using the following parameters: % identity and % similarity for a nucleotide sequence using GAP Weight of 50 and Length Weight of 3, and the nwsgapdna.cmp scoring matrix; % identity and % similarity for an amino acid sequence using GAP Weight of 8 and Length Weight of 2, and the BLOSUM62 scoring matrix; or any equivalent program thereof. By "equivalent program" is intended any sequence comparison program that, for any two sequences in question, generates an alignment having identical nucleotide or amino acid residue matches and an identical percent sequence identity when compared to the corresponding alignment generated by GAP Version 10.

GAP uses the algorithm of Needleman and Wunsch, (1970) $J.$ $Mol.$ $Biol.$ 48:443-453, to find the alignment of two complete sequences that maximizes the number of matches and minimizes the number of gaps. GAP considers all possible alignments and gap positions and creates the alignment with the largest number of matched bases and the fewest gaps. It allows for the provision of a gap creation penalty and a gap extension penalty in units of matched bases. GAP must make a profit of gap creation penalty number of matches for each gap it inserts. If a gap extension penalty greater than zero is chosen, GAP must, in addition, make a profit for each gap inserted of the length of the gap times the gap extension penalty. Default gap creation penalty values and gap extension penalty values in Version 10 of the GCG Wisconsin Genetics Software Package® for protein sequences are 8 and 2, respectively. For nucleotide sequences the default gap creation penalty is 50 while the default gap extension penalty is 3. The gap creation and gap extension penalties can be expressed as an integer selected from the group of integers consisting of from 0 to 200. Thus, for example, the gap creation and gap extension penalties can be 0, 1, 2, 3, 4, 5, 6, 7, 8, 9, 10, 15, 20, 25, 30, 35, 40, 45, 50, 55, 60, 65 or greater.

GAP presents one member of the family of best alignments. There may be many members of this family, but no other member has a better quality. GAP displays four figures of merit for alignments: Quality, Ratio, Identity and Similarity. The Quality is the metric maximized in order to align the sequences. Ratio is the quality divided by the number of bases in the shorter segment. Percent Identity is the percent of the symbols that actually match. Percent Similarity is the percent of the symbols that are similar. Symbols that are across from gaps are ignored. A similarity is scored when the scoring matrix value for a pair of symbols is greater than or equal to 0.50, the similarity threshold. The scoring matrix used in Version 10 of the GCG Wisconsin Genetics Software Package® is BLOSUM62 (see, Henikoff and Henikoff, (1989) $Proc.$ $Natl.$ $Acad.$ $Sci.$ $USA$ 89:10915).

(c) As used herein, "sequence identity" or "identity" in the context of two polynucleotides or polypeptide sequences makes reference to the residues in the two sequences that are the same when aligned for maximum correspondence over a specified comparison window. When percentage of sequence identity is used in reference to proteins it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule. When sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., as implemented in the program PC/GENE (Intelligenetics, Mountain View, Calif.).

(d) As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison and multiplying the result by 100 to yield the percentage of sequence identity.

B. Plants

In specific embodiments, the invention provides plants, plant cells and plant parts having altered levels (i.e., an increase or decrease) of an AP2 transcription factor sequence. In some embodiments, the plants and plant parts have stably incorporated into their genome at least one heterologous polynucleotide encoding an AP2 transcription factor polypeptide comprising the AP2 transcription factor domain as set forth in SEQ ID NO: 5, or a biologically active variant or fragment thereof. In one embodiment, the polynucleotide encoding the AP2 transcription factor polypeptide is set forth in SEQ ID NO: 1 or a biologically active variant or fragment thereof.

In yet other embodiments, plants and plant parts are provided in which the heterologous polynucleotide stably integrated into the genome of the plant or plant part comprises a polynucleotide which when expressed in a plant increases the level of an AP2 transcription factor polypeptide comprising an AP2 transcription factor domain, an AP2 transcription factor domain or an active variant or fragment thereof. Sequences that can be used to increase expression of an AP2 transcription factor polypeptide include, but are not limited to, the sequence set forth in SEQ ID NO: 1 or variants or fragments thereof.

As discussed in further detail elsewhere herein, such plants, plant cells, plant parts and seeds can have an altered phenotype including, for example, altered flower organ development, leaf formation, phototropism, apical dominance, fruit development, root initiation and improved yield.

As used herein, the term plant includes plant cells, plant protoplasts, plant cell tissue cultures from which plants can be regenerated, plant calli, plant clumps and plant cells that are intact in plants or parts of plants such as embryos, pollen, ovules, seeds, leaves, flowers, branches, fruit, kernels, ears, cobs, husks, stalks, roots, root tips, anthers and the like. Grain is intended to mean the mature seed produced by commercial growers for purposes other than growing or reproducing the species. Progeny, variants and mutants of the regenerated plants are also included within the scope of the invention, provided that these parts comprise the introduced or heterologous polynucleotides disclosed herein.

The present invention may be used for transformation of any plant species, including, but not limited to, monocots and dicots. Examples of plant species of interest include, but are not limited to, corn (*Zea mays*), *Brassica* sp. (e.g., *B. napus, B. rapa, B. juncea*), particularly those *Brassica* species useful as sources of seed oil, alfalfa (*Medicago sativa*), rice (*Oryza sativa*), rye (*Secale cereale*), sorghum (*Sorghum bicolor, Sorghum vulgare*), millet (e.g., pearl millet (*Pennisetum glaucum*), proso millet (*Panicum miliaceum*), foxtail millet (*Setaria italica*), finger millet (*Eleusine coracana*)), sunflower (*Helianthus annuus*), safflower (*Carthamus tinctorius*), wheat (*Triticum aestivum*), soybean (*Glycine max*), tobacco (*Nicotiana tabacum*), potato (*Solanum tuberosum*), peanuts (*Arachis hypogaea*), cotton (*Gossypium barbadense, Gossypium hirsutum*), sweet potato (*Ipomoea batatus*), cassava (*Manihot esculenta*), coffee (*Coffea* spp.), coconut (*Cocos nucifera*), pineapple (*Ananas comosus*), citrus trees (*Citrus* spp.), cocoa (*Theobroma cacao*), tea (*Camellia sinensis*), banana (*Musa* spp.), avocado (*Persea americana*), fig (*Ficus casica*), guava (*Psidium guajava*), mango (*Mangifera indica*), olive (*Olea europaea*), papaya (*Carica papaya*), cashew (*Anacardium occidentale*), macadamia (*Macadamia integrifolia*), almond (*Prunus amygdalus*), sugar beets (*Beta vulgaris*), sugarcane (*Saccharum* spp.), oats, barley, vegetables, ornamentals and conifers.

Vegetables include tomatoes (*Lycopersicon esculentum*), lettuce (e.g., *Lactuca sativa*), green beans (*Phaseolus vulgaris*), lima beans (*Phaseolus limensis*), peas (*Lathyrus* spp.) and members of the genus *Cucumis* such as cucumber (*C. sativus*), cantaloupe (*C. cantalupensis*) and musk melon (*C. melo*). Ornamentals include azalea (*Rhododendron* spp.), hydrangea (*Macrophylla hydrangea*), hibiscus (*Hibiscus rosasanensis*), roses (*Rosa* spp.), tulips (*Tulipa* spp.), daffodils (*Narcissus* spp.), petunias (*Petunia hybrida*), carnation (*Dianthus caryophyllus*), poinsettia (*Euphorbia pulcherrima*) and chrysanthemum.

Conifers that may be employed in practicing the present invention include, for example, pines such as loblolly pine (*Pinus taeda*), slash pine (*Pinus elliotii*), ponderosa pine (*Pinus ponderosa*), lodgepole pine (*Pinus contorta*) and Monterey pine (*Pinus radiata*); Douglas-fir (*Pseudotsuga menziesii*); Western hemlock (*Tsuga canadensis*); Sitka spruce (*Picea glauca*); redwood (*Sequoia sempervirens*); true firs such as silver fir (*Abies amabilis*) and balsam fir (*Abies balsamea*) and cedars such as Western red cedar (*Thuja plicata*) and Alaska yellow-cedar (*Chamaecyparis nootkatensis*). In specific embodiments, plants of the present invention are crop plants (for example, corn, alfalfa, sunflower, *Brassica*, soybean, cotton, safflower, peanut, sorghum, wheat, millet, tobacco, etc.). In other embodiments, corn and soybean plants are optimal and in yet other embodiments corn plants are optimal.

Other plants of interest include grain plants that provide seeds of interest, oil-seed plants, and leguminous plants. Seeds of interest include grain seeds, such as corn, wheat, barley, rice, sorghum, rye, etc. Oil-seed plants include cotton, soybean, safflower, sunflower, *Brassica*, maize, alfalfa, palm, coconut, etc. Leguminous plants include beans and peas. Beans include guar, locust bean, fenugreek, soybean, garden beans, cowpea, mungbean, lima bean, fava bean, lentils, chickpea, etc.

A "subject plant or plant cell" is one in which an alteration, such as transformation or introduction of a polypeptide, has occurred or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the alteration which resulted in the subject plant or cell; (b) a plant or plant cell of the same genotype as the starting material but which has been transformed with a null construct (i.e., with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest or (e) the subject plant or plant cell itself, under conditions in which the gene of interest is not expressed.

C. Polynucleotide Constructs

The use of the term "polynucleotide" is not intended to limit the present invention to polynucleotides comprising DNA. Those of ordinary skill in the art will recognize that polynucleotides, can comprise ribonucleotides and combinations of ribonucleotides and deoxyribonucleotides. Such deoxyribonucleotides and ribonucleotides include both naturally occurring molecules and synthetic analogues. The polynucleotides of the invention also encompass all forms of sequences including, but not limited to, single-stranded forms, double-stranded forms, hairpins, stem-and-loop structures and the like.

The various polynucleotides employed in the methods and compositions of the invention can be provided in expression cassettes for expression in the plant of interest. The cassette will include 5' and 3' regulatory sequences operably linked to a polynucleotide of the invention. "Operably linked" is intended to mean a functional linkage between two or more elements. For example, an operable linkage between a polynucleotide of interest and a regulatory sequence (i.e., a promoter) is functional link that allows for expression of the polynucleotide of interest. Operably linked elements may be contiguous or non-contiguous. When used to refer to the joining of two protein coding regions, by operably linked is intended that the coding regions are in the same reading frame. The cassette may additionally contain at least one additional gene to be cotransformed into the organism. Alternatively, the additional gene(s) can be provided on multiple expression cassettes. Such an expression cassette is provided with a plurality of restriction sites and/or recombination sites for insertion of the AP2 transcription factor polynucleotide to be under the transcriptional regulation of the regulatory regions. The expression cassette may additionally contain selectable marker genes.

The expression cassette can include in the 5'-3' direction of transcription, a transcriptional and translational initiation region (i.e., a promoter), an AP2 transcription factor polynucleotide and a transcriptional and translational termination region (i.e., termination region) functional in plants. The regulatory regions (i.e., promoters, transcriptional regulatory regions, and translational termination regions) and/or the AP2 transcription factor polynucleotide may be native/analogous to the host cell or to each other. Alternatively, the regulatory regions and/or the AP2 transcription factor polynucleotides may be heterologous to the host cell or to each other. As used herein, "heterologous" in reference to a sequence is a sequence that originates from a foreign species, or, if from the same species, is substantially modified from its native form in composition and/or genomic locus by deliberate human intervention. For example, a promoter operably linked to a heterologous polynucleotide is from a species different from the species from which the polynucleotide was derived or, if from the same/analogous species, one or both are substantially modified from their original form and/or genomic locus or the promoter is not the native promoter for the operably linked polynucleotide. As used herein, a chimeric gene comprises a coding sequence operably linked to a transcription initiation region that is heterologous to the coding sequence.

While it may be optimal to express the sequences using heterologous promoters, the native promoter sequences may be used. Such constructs can change expression levels of an AP2 transcription factor transcript or protein in the plant or plant cell. Thus, the phenotype of the plant or plant cell can be altered.

The termination region may be native with the transcriptional initiation region, may be native with the operably linked AP2 transcription factor polynucleotide of interest, may be native with the plant host, or may be derived from another source (i.e., foreign or heterologous) to the promoter, the AP2 transcription factor polynucleotide of interest, the plant host, or any combination thereof. Convenient termination regions are available from the Ti-plasmid of *A. tumefaciens*, such as the octopine synthase and nopaline synthase termination regions. See also, Guerineau, et al., (1991) *Mol. Gen. Genet.* 262:141-144; Proudfoot, (1991) *Cell* 64:671-674; Sanfacon, et al., (1991) *Genes Dev.* 5:141-149; Mogen, et al., (1990) *Plant Cell* 2:1261-1272; Munroe, et al., (1990) *Gene* 91:151-158; Ballas, et al., (1989) *Nucleic Acids Res.* 17:7891-7903 and Joshi, et al., (1987) *Nucleic Acids Res.* 15:9627-9639.

Where appropriate, the polynucleotides may be optimized for increased expression in the transformed plant. That is, the polynucleotides can be synthesized using plant-preferred codons for improved expression. See, for example, Campbell and Gowri, (1990) *Plant Physiol.* 92:1-11 for a discussion of host-preferred codon usage. Methods are available in the art for synthesizing plant-preferred genes. See, for example, U.S. Pat. Nos. 5,380,831 and 5,436,391 and Murray, et al., (1989) *Nucleic Acids Res.* 17:477-498, herein incorporated by reference.

Additional sequence modifications are known to enhance gene expression in a cellular host. These include elimination of sequences encoding spurious polyadenylation signals, exon-intron splice site signals, transposon repeats and other such well-characterized sequences that may be deleterious to gene expression. The G-C content of the sequence may be adjusted to levels average for a given cellular host, as calculated by reference to known genes expressed in the host cell. When possible, the sequence is modified to avoid predicted hairpin secondary mRNA structures.

The expression cassettes may additionally contain 5' leader sequences. Such leader sequences can act to enhance translation. Translation leaders are known in the art and include: picornavirus leaders, for example, EMCV leader (Encephalomyocarditis 5' noncoding region) (Elroy-Stein, et al., (1989) *Proc. Natl. Acad. Sci. USA* 86:6126-6130); potyvirus leaders, for example, TEV leader (Tobacco Etch Virus) (Gallie, et al., (1995) *Gene* 165(2):233-238), MDMV leader (Maize Dwarf Mosaic Virus) (*Virology* 154:9-20), and human immunoglobulin heavy-chain binding protein (BiP) (Macejak, et al., (1991) *Nature* 353:90-94); untranslated leader from the coat protein mRNA of alfalfa mosaic virus (AMV RNA 4) (Jobling, et al., (1987) *Nature* 325:622-625); tobacco mosaic virus leader (TMV) (Gallie, et al., (1989) in *Molecular Biology of RNA*, ed. Cech (Liss, New York), pp. 237-256); and maize chlorotic mottle virus leader (MCMV) (Lommel, et al., (1991) *Virology* 81:382-385). See also, Della-Cioppa, et al., (1987) *Plant Physiol.* 84:965-968.

In preparing the expression cassette, the various DNA fragments may be manipulated, so as to provide for the DNA sequences in the proper orientation and, as appropriate, in the proper reading frame. Toward this end, adapters or linkers may be employed to join the DNA fragments or other manipulations may be involved to provide for convenient restriction sites, removal of superfluous DNA, removal of restriction sites or the like. For this purpose, in vitro mutagenesis, primer repair, restriction, annealing, resubstitutions, e.g., transitions and transversions, may be involved.

A number of promoters can be used in the practice of the invention, including the native promoter of the polynucleotide sequence of interest. The promoters can be selected based on the desired outcome. The nucleic acids can be combined with constitutive, tissue-preferred or other promoters for expression in plants.

Such constitutive promoters include, for example, the core promoter of the Rsyn7 promoter and other constitutive promoters disclosed in WO 99/43838 and U.S. Pat. No. 6,072,050; the core CaMV 35S promoter (Odell, et al., (1985) *Nature* 313:810-812); rice actin (McElroy, et al., (1990) *Plant Cell* 2:163-171); ubiquitin (Christensen, et al., (1989) *Plant Mol. Biol.* 12:619-632 and Christensen, et al., (1992) *Plant Mol. Biol.* 18:675-689); pEMU (Last, et al., (1991) *Theor. Appl. Genet.* 81:581-588); MAS (Velten, et al., (1984) *EMBO J.* 3:2723-2730); ALS promoter (U.S. Pat. No. 5,659,026), GOS2 promoter (dePater, et al., (1992) *Plant J.* 2:837-44) and the like. Other constitutive promoters include, for example, U.S. Pat. Nos. 5,608,149; 5,608,144; 5,604,121; 5,569,597; 5,466,785; 5,399,680; 5,268,463; 5,608,142 and 6,177,611.

The expression cassette can also comprise a selectable marker gene for the selection of transformed cells. Selectable marker genes are utilized for the selection of transformed cells or tissues. Marker genes include genes encoding antibiotic resistance, such as those encoding neomycin phosphotransferase II (NEO) and hygromycin phosphotransferase (HPT), as well as genes conferring resistance to herbicidal compounds, such as glufosinate ammonium, bromoxynil, imidazolinones, and 2,4-dichlorophenoxyacetate (2,4-D). Additional selectable markers include phenotypic markers such as β-galactosidase and fluorescent proteins such as green fluorescent protein (GFP) (Su, et al., (2004) *Biotechnol Bioeng* 85:610-9 and Fetter, et al., (2004) *Plant Cell* 16.215-28), cyan florescent protein (CYP) (Bolte, et al., (2004) *J. Cell Science* 117:943-54 and Kato, et al., (2002) *Plant Physiol* 129:913-42) and yellow florescent protein (PhiYFP™ from Evrogen, see, Bolte, et al., (2004) *J. Cell Science* 117:943-54). For additional selectable markers, see generally, Yarranton, (1992) *Curr. Opin. Biotech.* 3:506-511; Christopherson, et al., (1992) *Proc. Natl. Acad. Sci. USA* 89:6314-6318; Yao, et al., (1992) *Cell* 71:63-72; Reznikoff, (1992) *Mol. Microbiol.* 6:2419-2422; Barkley, et al., (1980) in *The Operon, pp.* 177-220; Hu, et al., (1987) *Cell* 48:555-566; Brown, et al., (1987) *Cell* 49:603-612; Figge, et al., (1988) *Cell* 52:713-722; Deuschle, et al., (1989) *Proc. Natl. Acad. Aci. USA* 86:5400-5404; Fuerst, et al., (1989) *Proc. Natl. Acad. Sci. USA* 86:2549-2553; Deuschle, et al., (1990) *Science* 248:480-483; Gossen, (1993) Ph.D. Thesis, University of Heidelberg; Reines, et al., (1993) *Proc. Natl. Acad. Sci. USA* 90:1917-1921; Labow, et al., (1990) *Mol. Cell. Biol.* 10:3343-3356; Zambretti, et al., (1992) *Proc. Natl. Acad. Sci. USA* 89:3952-3956; Baim, et al., (1991) *Proc. Natl. Acad. Sci. USA* 88:5072-5076; Wyborski, et al., (1991) *Nucleic Acids Res.* 19:4647-4653; Hillenand-Wissman, (1989) *Topics Mol. Struc. Biol.* 10:143-162; Degenkolb, et al., (1991) *Antimi-* crob. Agents Chemother. 35:1591-1595; Kleinschnidt, et al., (1988) Biochemistry 27:1094-1104; Bonin, (1993) Ph.D. Thesis, University of Heidelberg; Gossen, et al., (1992) Proc. Natl. Acad. Sci. USA 89:5547-5551; Oliva, et al., (1992) Antimicrob. Agents Chemother. 36:913-919; Hlavka, et al., (1985) Handbook of Experimental Pharmacology, Vol. 78 (Springer-Verlag, Berlin); Gill, et al., (1988) Nature 334:721-724. Such disclosures are herein incorporated by reference. The above list of selectable marker genes is not meant to be limiting. Any selectable marker gene can be used in the present invention.

In certain embodiments the polynucleotides of the present invention can be stacked with any combination of polynucleotide sequences of interest in order to create plants with a desired trait. A trait, as used herein, refers to the phenotype derived from a particular sequence or groups of sequences. The combinations generated can also include multiple copies of any one of the polynucleotides of interest. The polynucleotides of the present invention can also be stacked with traits desirable for disease or herbicide resistance (e.g., fumonisin detoxification genes (U.S. Pat. No. 5,792,931); avirulence and disease resistance genes (Jones, et al., (1994) Science 266:789; Martin, et al., (1993) Science 262:1432; Mindrinos, et al., (1994) Cell 78:1089); acetolactate synthase (ALS) mutants that lead to herbicide resistance such as the S4 and/or Hra mutations; inhibitors of glutamine synthase such as phosphinothricin or basta (e.g., bar gene); and glyphosate resistance (EPSPS gene)) and traits desirable for processing or process products such as high oil (e.g., U.S. Pat. No. 6,232, 529); modified oils (e.g., fatty acid desaturase genes (U.S. Pat. No. 5,952,544; WO 94/11516)); modified starches (e.g., ADPG pyrophosphorylases (AGPase), starch synthases (SS), starch branching enzymes (SBE), and starch debranching enzymes (SDBE)) and polymers or bioplastics (e.g., U.S. Pat. No. 5,602,321; beta-ketothiolase, polyhydroxybutyrate synthase, and acetoacetyl-CoA reductase (Schubert, et al., (1988) J. Bacteriol. 170:5837-5847) facilitate expression of polyhydroxyalkanoates (PHAs)), the disclosures of which are herein incorporated by reference. One could also combine the polynucleotides of the present invention with polynucleotides providing agronomic traits such as male sterility (e.g., see, U.S. Pat. No. 5,583,210), stalk strength, flowering time or transformation technology traits such as cell cycle regulation or gene targeting (e.g., WO 99/61619, WO 00/17364, and WO 99/25821), the disclosures of which are herein incorporated by reference.

These stacked combinations can be created by any method including, but not limited to, cross-breeding plants by any conventional or TopCross methodology or genetic transformation. If the sequences are stacked by genetically transforming the plants, the polynucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate transformation cassettes (trans) or contained on the same transformation cassette (cis). Expression of the sequences can be driven by the same promoter or by different promoters. In certain cases, it may be desirable to introduce a transformation cassette that will suppress the expression of the polynucleotide of interest. This may be combined with any combination of other suppression cassettes or overexpression cassettes to generate the desired combination of traits in the plant. It is further recognized that polynucleotide sequences can be stacked at a desired genomic location using a site-specific recombination system. See, for example, WO99/25821, WO99/25854, WO99/25840, WO99/25855 and WO99/25853, all of which are herein incorporated by reference.

D. Method of Introducing

The methods of the invention involve introducing a polypeptide or polynucleotide into a plant. "Introducing" is intended to mean presenting to the plant the polynucleotide or polypeptide in such a manner that the sequence gains access to the interior of a cell of the plant. The methods of the invention do not depend on a particular method for introducing a sequence into a plant, only that the polynucleotide or polypeptides gains access to the interior of at least one cell of the plant. Methods for introducing polynucleotide or polypeptides into plants are known in the art including, but not limited to, stable transformation methods, transient transformation methods and virus-mediated methods.

"Stable transformation" is intended to mean that the nucleotide construct introduced into a plant integrates into the genome of the plant and is capable of being inherited by the progeny thereof. "Transient transformation" is intended to mean that a polynucleotide is introduced into the plant and does not integrate into the genome of the plant or a polypeptide is introduced into a plant.

Transformation protocols as well as protocols for introducing polypeptides or polynucleotide sequences into plants may vary depending on the type of plant or plant cell, i.e., monocot or dicot, targeted for transformation. Suitable methods of introducing polypeptides and polynucleotides into plant cells include microinjection (Crossway, et al., (1986) Biotechniques 4:320-334), electroporation (Riggs, et al., (1986) Proc. Natl. Acad. Sci. USA 83:5602-5606, Agrobacterium-mediated transformation (U.S. Pat. No. 5,563,055 and U.S. Pat. No. 5,981,840), direct gene transfer (Paszkowski, et al., (1984) EMBO J. 3:2717-2722) and ballistic particle acceleration (see, for example, U.S. Pat. No. 4,945,050; U.S. Pat. No. 5,879,918; U.S. Pat. Nos. 5,886,244 and 5,932,782; Tomes, et al., (1995) in Plant Cell, Tissue, and Organ Culture: Fundamental Methods, ed. Gamborg and Phillips, (Springer-Verlag, Berlin); McCabe, et al., (1988) Biotechnology 6:923-926) and Lec1 transformation (WO 00/28058). Also see, Weissinger, et al., (1988) Ann. Rev. Genet. 22:421-477; Sanford, et al., (1987) Particulate Science and Technology 5:27-37 (onion); Christou, et al., (1988) Plant Physiol. 87:671-674 (soybean); McCabe, et al., (1988) Bio/Technology 6:923-926 (soybean); Finer and McMullen, (1991) In Vitro Cell Dev. Biol. 27P:175-182 (soybean); Singh, et al., (1998) Theor. Appl. Genet. 96:319-324 (soybean); Datta, et al., (1990) Biotechnology 8:736-740 (rice); Klein, et al., (1988) Proc. Natl. Acad. Sci. USA 85:4305-4309 (maize); Klein, et al., (1988) Biotechnology 6:559-563 (maize); U.S. Pat. Nos. 5,240,855; 5,322,783 and 5,324,646; Klein, et al., (1988) Plant Physiol. 91:440-444 (maize); Fromm, et al., (1990) Biotechnology 8:833-839 (maize); Hooykaas-Van Slogteren, et al., (1984) Nature (London) 311:763-764; U.S. Pat. No. 5,736,369 (cereals); Bytebier, et al., (1987) Proc. Natl. Acad. Sci. USA 84:5345-5349 (Liliaceae); De Wet, et al., (1985) in The Experimental Manipulation of Ovule Tissues, ed. Chapman, et al., (Longman, N.Y.), pp. 197-209 (pollen); Kaeppler, et al., (1990) Plant Cell Reports 9:415-418 and Kaeppler, et al., (1992) Theor. Appl. Genet. 84:560-566 (whisker-mediated transformation); D'Halluin, et al., (1992) Plant Cell 4:1495-1505 (electroporation); Li, et al., (1993) Plant Cell Reports 12:250-255 and Christou and Ford, (1995) Annals of Botany 75:407-413 (rice); Osjoda, et al., (1996) Nature Biotechnol-

*ogy* 14:745-750 (maize via *Agrobacterium tumefaciens*), all of which are herein incorporated by reference.

In specific embodiments, the AP2 transcription factor sequences or variants and fragments thereof can be provided to a plant using a variety of transient transformation methods. Such transient transformation methods include, but are not limited to, the introduction of the AP2 transcription factor protein or variants and fragments thereof directly into the plant or the introduction of the AP2 transcription factor transcript into the plant. Such methods include, for example, microinjection or particle bombardment. See, for example, Crossway, et al., (1986) *Mol Gen. Genet.* 202:179-185; Nomura, et al., (1986) *Plant Sci.* 44:53-58; Hepler, et al., (1994) *Proc. Natl. Acad. Sci.* 91:2176-2180 and Hush, et al., (1994) *The Journal of Cell Science* 107:775-784, all of which are herein incorporated by reference. Alternatively, the AP2 transcription factor polynucleotide can be transiently transformed into the plant using techniques known in the art. Such techniques include viral vector system and the precipitation of the polynucleotide in a manner that precludes subsequent release of the DNA. Thus, the transcription from the particle-bound DNA can occur, but the frequency with which it is released to become integrated into the genome is greatly reduced. Such methods include the use particles coated with polyethylamine (PEI; Sigma #P3143).

In other embodiments, the polynucleotide of the invention may be introduced into plants by contacting plants with a virus or viral nucleic acids. Generally, such methods involve incorporating a nucleotide construct of the invention within a viral DNA or RNA molecule. It is recognized that the an AP2 transcription factor sequence or a variant or fragment thereof may be initially synthesized as part of a viral polyprotein, which later may be processed by proteolysis in vivo or in vitro to produce the desired recombinant protein. Further, it is recognized that promoters of the invention also encompass promoters utilized for transcription by viral RNA polymerases. Methods for introducing polynucleotides into plants and expressing a protein encoded therein, involving viral DNA or RNA molecules, are known in the art. See, for example, U.S. Pat. Nos. 5,889,191, 5,889,190, 5,866,785, 5,589,367, 5,316,931 and Porta, et al., (1996) *Molecular Biotechnology* 5:209-221, herein incorporated by reference.

Methods are known in the art for the targeted insertion of a polynucleotide at a specific location in the plant genome. In one embodiment, the insertion of the polynucleotide at a desired genomic location is achieved using a site-specific recombination system. See, for example, WO99/25821, WO99/25854, WO99/25840, WO99/25855, and WO99/25853, all of which are herein incorporated by reference. Briefly, the polynucleotide of the invention can be contained in transfer cassette flanked by two non-recombinogenic recombination sites. The transfer cassette is introduced into a plant having stably incorporated into its genome a target site which is flanked by two non-recombinogenic recombination sites that correspond to the sites of the transfer cassette. An appropriate recombinase is provided and the transfer cassette is integrated at the target site. The polynucleotide of interest is thereby integrated at a specific chromosomal position in the plant genome.

The cells that have been transformed may be grown into plants in accordance with conventional ways. See, for example, McCormick, et al., (1986) *Plant Cell Reports* 5:81-84. These plants may then be grown, and either pollinated with the same transformed strain or different strains, and the resulting progeny having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present invention provides transformed seed (also referred to as "transgenic seed") having a polynucleotide of the invention, for example, an expression cassette of the invention, stably incorporated into their genome.

III. Methods of Use

A. Methods for Modulating Expression of at Least One AP2 Transcription Factor Sequence or a Variant or Fragment Therefore in a Plant or Plant Part A "modulated level" or "modulating level" of a polypeptide in the context of the methods of the present invention refers to any increase or decrease in the expression, concentration or activity of a gene product, including any relative increment in expression, concentration or activity. Any method or composition that modulates expression of a target gene product, either at the level of transcription or translation or modulates the activity of the target gene product can be used to achieve modulated expression, concentration, activity of the target gene product. In general, the level is increased or decreased by at least 1%, 5%, 10%, 20%, 30%, 40%, 50%, 60%, 70%, 80%, 90% or greater relative to an appropriate control plant, plant part, or cell. Modulation in the present invention may occur during and/or subsequent to growth of the plant to the desired stage of development. In specific embodiments, the polypeptides of the present invention are modulated in monocots, particularly grain plants such as rice, wheat, maize and the like.

The expression level of a polypeptide having an AP2 transcription factor domain or a biologically active variant or fragment thereof may be measured directly, for example, by assaying for the level of the AP2 transcription factor polypeptide in the plant or indirectly, for example, by measuring the level of the polynucleotide encoding the protein or by measuring the activity of the AP2 transcription factor polypeptide in the plant. Methods for determining the activity of the AP2 transcription factor polypeptide are described elsewhere herein.

In specific embodiments, the polypeptide or the polynucleotide of the invention is introduced into the plant cell. Subsequently, a plant cell having the introduced sequence of the invention is selected using methods known to those of skill in the art such as, but not limited to, Southern blot analysis, DNA sequencing, PCR analysis, or phenotypic analysis. A plant or plant part altered or modified by the foregoing embodiments is grown under plant forming conditions for a time sufficient to modulate the concentration and/or activity of polypeptides of the present invention in the plant. Plant forming conditions are well known in the art and discussed briefly elsewhere herein.

It is also recognized that the level and/or activity of the polypeptide may be modulated by employing a polynucleotide that is not capable of directing, in a transformed plant, the expression of a protein or an RNA. For example, the polynucleotides of the invention may be used to design polynucleotide constructs that can be employed in methods for altering or mutating a genomic nucleotide sequence in an organism. Such polynucleotide constructs include, but are not limited to, RNA:DNA vectors, RNA:DNA mutational vectors, RNA:DNA repair vectors, mixed-duplex oligonucleotides, self-complementary RNA:DNA oligonucleotides and recombinogenic oligonucleobases. Such nucleotide constructs and methods of use are known in the art. See, U.S. Pat. Nos. 5,565,350; 5,731,181; 5,756,325; 5,760,012; 5,795,972 and 5,871,984, all of which are herein incorporated by reference. See also, WO 98/49350, WO 99/07865, WO 99/25821 and Beetham, et al., (1999) *Proc. Natl. Acad. Sci. USA* 96:8774-8778, herein incorporated by reference.

It is therefore recognized that methods of the present invention do not depend on the incorporation of the entire polynucleotide into the genome, only that the plant or cell thereof is altered as a result of the introduction of the polynucleotide into a cell. In one embodiment of the invention, the genome may be altered following the introduction of the polynucleotide into a cell. For example, the polynucleotide, or any part thereof, may incorporate into the genome of the plant. Alterations to the genome of the present invention include, but are not limited to, additions, deletions and substitutions of nucleotides into the genome. While the methods of the present invention do not depend on additions, deletions, and substitutions of any particular number of nucleotides, it is recognized that such additions, deletions, or substitutions comprises at least one nucleotide.

In one embodiment, the activity and/or level of an AP2 transcription factor polypeptide is increased. An increase in the level and/or activity of the AP2 transcription factor polypeptide can be achieved by providing to the plant an AP2 transcription factor polypeptide or a biologically active variant or fragment thereof. As discussed elsewhere herein, many methods are known in the art for providing a polypeptide to a plant including, but not limited to, direct introduction of the AP2 transcription factor polypeptide into the plant or introducing into the plant (transiently or stably) a polynucleotide construct encoding a polypeptide having AP2 transcription factor activity. It is also recognized that the methods of the invention may employ a polynucleotide that is not capable of directing in the transformed plant the expression of a protein or an RNA. Thus, the level and/or activity of an AP2 transcription factor polypeptide may be increased by altering the gene encoding the AP2 transcription factor polypeptide or its promoter. See, e.g., Kmiec, U.S. Pat. No. 5,565,350; Zarling, et al., PCT/US93/03868. Therefore, mutagenized plants that carry mutations in AP2 transcription factor genes, where the mutations increase expression of the AP2 transcription factor gene or increase the activity of the encoded AP2 transcription factor polypeptide, are provided.

In other embodiments, the activity and/or level of the AP2 transcription factor polypeptide of the invention is reduced or eliminated by introducing into a plant a polynucleotide that inhibits the level or activity of a polypeptide. The polynucleotide may inhibit the expression of AP2 transcription factor gene directly, by preventing translation of the AP2 transcription factor messenger RNA, or indirectly, by encoding a polypeptide that inhibits the transcription or translation of an AP2 transcription factor gene encoding an AP2 transcription factor protein. Methods for inhibiting or eliminating the expression of a gene in a plant are well known in the art, and any such method may be used in the present invention to inhibit the expression of at least one AP2 transcription factor sequence in a plant. In other embodiments of the invention, the activity of an AP2 transcription factor polypeptide is reduced or eliminated by transforming a plant cell with a sequence encoding a polypeptide that inhibits the activity of the AP2 transcription factor polypeptide. In other embodiments, the activity of an AP2 transcription factor polypeptide may be reduced or eliminated by disrupting the gene encoding the AP2 transcription factor polypeptide. The invention encompasses mutagenized plants that carry mutations in AP2 transcription factor genes, where the mutations reduce expression of the AP2 transcription factor gene or inhibit the AP2 transcription factor activity of the encoded AP2 transcription factor polypeptide.

Reduction of the activity of specific genes (also known as gene silencing or gene suppression) is desirable for several aspects of genetic engineering in plants. Many techniques for gene silencing are well known to one of skill in the art, including, but not limited to, antisense technology (see, e.g., Sheehy, et al., (1988) *Proc. Natl. Acad. Sci. USA* 85:8805-8809 and U.S. Pat. Nos. 5,107,065; 5,453,566 and 5,759,829); cosuppression (e.g., Taylor, (1997) *Plant Cell* 9:1245; Jorgensen, (1990) *Trends Biotech.* 8(12):340-344; Flavell, (1994) *Proc. Natl. Acad. Sci. USA* 91:3490-3496; Finnegan, et al., (1994) *Bio/Technology* 12:883-888; and Neuhuber, et al., (1994) *Mol. Gen. Genet.* 244:230-241); RNA interference (Napoli, et al., (1990) *Plant Cell* 2:279-289; U.S. Pat. No. 5,034,323; Sharp, (1999) *Genes Dev.* 13:139-141; Zamore, et al., (2000) *Cell* 101:25-33 and Montgomery, et al., (1998) *Proc. Natl. Acad. ScL USA* 95:15502-15507), virus-induced gene silencing (Burton, et al., (2000) *Plant Cell* 12:691-705; and Baulcombe, (1999) *Curr. Op. Plant Bio.* 2:109-113); target-RNA-specific ribozymes (Haseloff, et al., (1988) *Nature* 334:585-591); hairpin structures (Smith, et al., (2000) *Nature* 407:319-320; WO 99/53050; WO 02/00904; WO 98/53083; Chuang and Meyerowitz, (2000) *Proc. Natl. Acad. Sci. USA* 97:4985-4990; Stoutjesdijk, et al., (2002) *Plant Physiol.* 129:1723-1731; Waterhouse and Helliwell, (2003) *Nat. Rev. Genet.* 4:29-38; Pandolfini, et al., *BMC Biotechnology* 3:7, US Patent Application Publication Number 2003/0175965; Panstruga, et al., (2003) *Mol. Biol. Rep.* 30:135-140; Wesley, et al., (2001) *Plant J.* 27:581-590; Wang and Waterhouse, (2001) *Curr. Opin. Plant Biol.* 5:146-150; US Patent Application Publication Number 2003/0180945; and, WO 02/00904, all of which are herein incorporated by reference); ribozymes (Steinecke, et al., (1992) *EMBO J.* 11:1525; and Perriman, et al., (1993) *Antisense Res. Dev.* 3:253); oligonucleotide-mediated targeted modification (e.g., WO 03/076574 and WO 99/25853); Zn-finger targeted molecules (e.g., WO 01/52620; WO 03/048345; and WO 00/42219); transposon tagging (Maes, et al., (1999) *Trends Plant Sci.* 4:90-96; Dharmapuri and Sonti, (1999) *FEMS Microbiol. Lett.* 179:53-59; Meissner, et al., (2000) *Plant J.* 22:265-274; Phogat, et al., (2000) *J. Biosci.* 25:57-63; Walbot, (2000) *Curr. Opin. Plant Biol.* 2:103-107; Gai, et al., (2000) *Nucleic Acids Res.* 28:94-96; Fitzmaurice, et al., (1999) *Genetics* 153:1919-1928; Bensen, et al., (1995) *Plant Cell* 7:75-84; Mena, et al., (1996) *Science* 274:1537-1540 and U.S. Pat. No. 5,962,764); each of which is herein incorporated by reference; and other methods or combinations of the above methods known to those of skill in the art.

It is recognized that with the polynucleotides of the invention, antisense constructions, complementary to at least a portion of the messenger RNA (mRNA) for the AP2 transcription factor sequences can be constructed. Antisense nucleotides are constructed to hybridize with the corresponding mRNA. Modifications of the antisense sequences may be made as long as the sequences hybridize to and interfere with expression of the corresponding mRNA. In this manner, antisense constructions having 70%, optimally 80%, more optimally 85% sequence identity to the corresponding antisensed sequences may be used. Furthermore, portions of the antisense nucleotides may be used to disrupt the expression of the target gene. Generally, sequences of at least 50 nucleotides, 100 nucleotides, 200 nucleotides, 300, 400, 450, 500, 550 or greater may be used.

The polynucleotides of the present invention may also be used in the sense orientation to suppress the expression of endogenous genes in plants. Methods for suppressing gene expression in plants using polynucleotides in the sense orientation are known in the art. The methods generally involve transforming plants with a DNA construct comprising a promoter that drives expression in a plant operably linked to at least a portion of a polynucleotide that corresponds to the transcript of the endogenous gene. Typically, such a nucleotide sequence has substantial sequence identity to the sequence of the transcript of the endogenous gene, optimally greater than about 65% sequence identity, more optimally greater than about 85% sequence identity, most optimally greater than about 95% sequence identity. See, U.S. Pat. Nos. 5,283,184 and 5,034,323; herein incorporated by reference.

Thus, many methods may be used to reduce or eliminate the activity of an AP2 transcription factor polypeptide or a biologically active variant or fragment thereof. In addition, combinations of methods may be employed to reduce or eliminate the activity of at least one AP2 transcription factor polypeptide. It is further recognized that the level of a single AP2 transcription factor sequence can be modulated to produce the desired phenotype. Alternatively, is may be desirable to modulate (increase and/or decrease) the level of expression of multiple sequences having an AP2 transcription factor domain or a biologically active variant or fragment thereof.

As discussed above, a variety of promoters can be employed to modulate the level of the AP2 transcription factor sequence. In one embodiment, the expression of the heterologous polynucleotide which modulates the level of at least one AP2 transcription factor polypeptide can be regulated by a tissue-preferred promoter, particularly, a leaf-preferred promoter (i.e., mesophyll-preferred promoter or a bundle sheath preferred promoter) and/or a seed-preferred promoter (i.e., an endosperm-preferred promoter or an embryo-preferred promoter).

B. Methods to Modulate Floral Organ Development and Yield in a Plant

Auxin flux is implicated in patterning, initiation and growth of floral organs by genetic and physiological analyses. The ETTIN/ARF3 transcription factor responds to auxin to affect perianth organ number and reproductive organ differentiation in the *Arabidopsis* flower (Pfluger and Zambryski, (2004) *Development* 131:4697-4707). The AP2 transcription factor nucleic acid molecules of the invention encode a protein that may transcriptionally co-repress the AGAMOUS floral organ identity gene. Additionally, AP2 transcription factor may play a role in auxin-regulated growth and development. AP2 transcription factor has a pleiotropic phenotype that includes reductions in several classic auxin responses such as apical dominance, lateral root initiation, sensitivity to exogenous auxin and activation of the DR5 auxin response reporter.

Accordingly, methods and compositions are provided to modulate AP2 transcription factor and AP2 transcription factor polypeptides and thus to modulate floral organ development, root initiation, and yield in plants. In one embodiment, the compositions of the invention can be used to increase grain yield in cereal plants. In this embodiment, the AP2 transcription factor coding sequence is expressed in a cereal plant of interest to increase expression of the AP2 transcription factor transcription factor.

In this manner, the methods and compositions can be used to increase yield in a plant. As used herein, the term "improved yield" means any improvement in the yield of any measured plant product. The improvement in yield can comprise a 0.1%, 0.5%, 1%, 3%, 5%, 10%, 15%, 20%, 30%, 40%, 50%, 60%, 70%, 80%, 90% or greater increase in measured plant product. Alternatively, the increased plant yield can comprise about a 0.5 fold, 1 fold, 2 fold, 4 fold, 8 fold, 16 fold or 32 fold increase in measured plant products. For example, an increase in the bu/acre yield of soybeans or corn derived from a crop having the present treatment as compared with the bu/acre yield from untreated soybeans or corn cultivated under the same conditions would be considered an improved yield. By increased yield is also intended at least one of an increase in total seed numbers, an increase in total seed weight, an increase in root biomass and an increase in harvest index. Harvest index is defined as the ratio of yield biomass to the total cumulative biomass at harvest.

Accordingly, various methods to increase yield of a plant are provided. In one embodiment, increasing yield of a plant or plant part comprises introducing into the plant or plant part a heterologous polynucleotide and expressing the heterologous polynucleotide in the plant or plant part. In this method, the expression of the heterologous polynucleotide modulates the level of at least one AP2 transcription factor polypeptide in the plant or plant part, where the AP2 transcription factor polypeptide comprises an AP2 transcription factor domain (or both) having an amino acid sequence set forth in SEQ ID NO: 5 (AP2 transcription factor domain) or SEQ ID NO: 6 (polyglycine) or SEQ ID NOS: 7-11 (polyserine domains), or a variant or fragment of the domain.

In specific embodiments, modulation of the level of the AP2 transcription factor polypeptide comprises an increase in the level of at least one AP2 transcription factor polypeptide. In such methods, the heterologous polynucleotide introduced into the plant encodes a polypeptide having an AP2 transcription factor domain or a biologically active variant or fragment thereof. In specific embodiments, the heterologous polynucleotide comprises the sequence set forth in at least one SEQ ID NO: 1 and/or a biologically active variant or fragment thereof.

In other embodiments, modulating the level of at least one AP2 transcription factor polypeptide comprises decreasing in the level of at least one AP2 transcription factor polypeptide. In such methods, the heterologous polynucleotide introduced into the plant need not encode a functional AP2 transcription factor polypeptide, but rather the expression of the polynucleotide results in the decreased expression of an AP2 transcription factor polypeptide comprising an AP2 transcription factor domain or a biologically active variant or fragment of the AP2 transcription factor domain. In specific embodiments, the AP2 transcription factor polypeptide having the decreased level is set forth in at least one of SEQ ID NO: 2 or SEQ ID NO: 4 or a biologically active variant or fragment thereof.

The following examples are offered by way of illustration and not by way of limitation.

EXPERIMENTAL

Example 1

Cloning of AP2 Transcription Factor Gene

The cDNA that encoded the AP2 transcription factor polypeptide from *Arabidopsis* was identified by screening a population of activation tagged *Arabidopsis* plants for phenotypic variants with altered yield components. The AP2 gene was cloned by inverse PCR (iPCR) using primers designed to the activation tag. Activation of AP2 was verified by quantifying AP2 mRNA by RT-PCR. The phenotype of ectopic/overexpression of AP2 was confirmed by cloning the genomic (intron containing) and cDNA versions of the AP2 gene in a transgene cassette with constitutive promoters (SCP PRO) and the *Arabidopsis* Ubiquitin 10 promoter (AT-UBQ10) and transforming wild-type *Arabidopsis* (Columbia ecotype).

Figure 7:
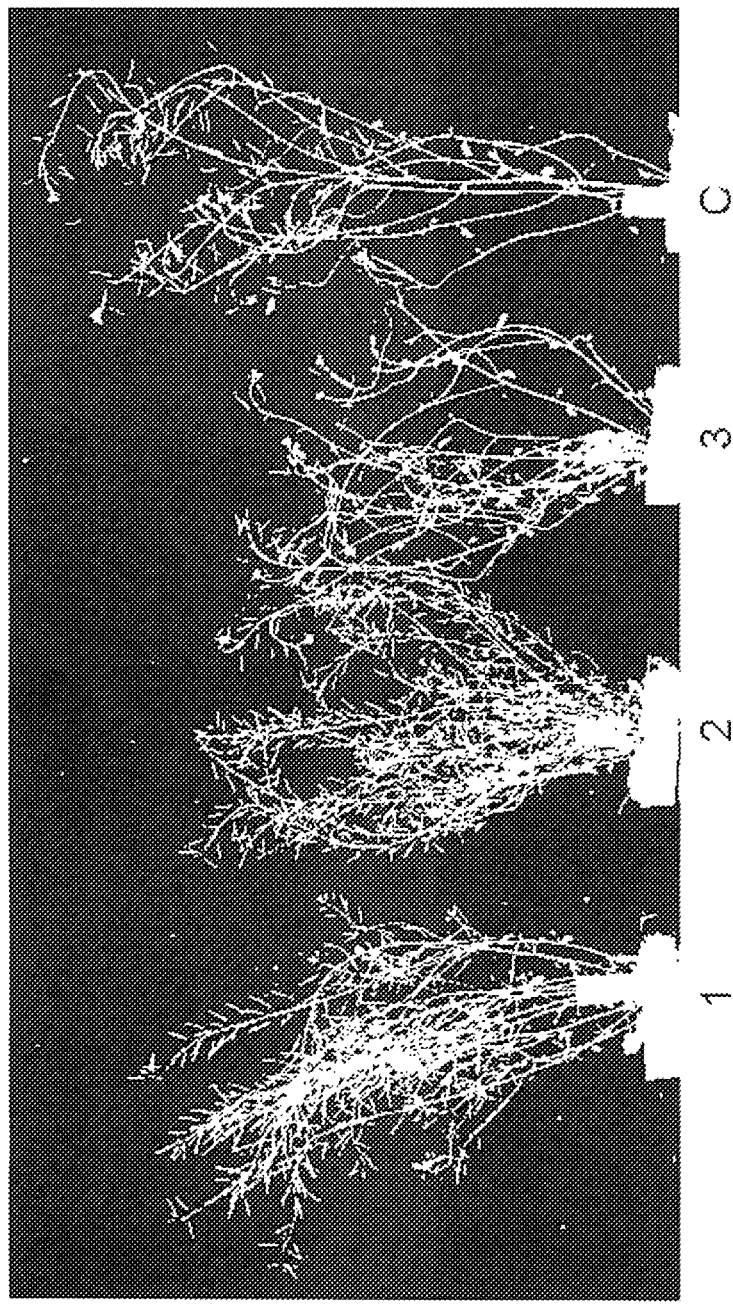
FIG. 7. Plants over-expressing AT-AP2 have increased bolt number and silique number. Three transgenic plants over-expressing the AT-AP2 gene are shown (plants 1-3) relative to a non-transgenic wild-type control plant (C).
Figure 8:
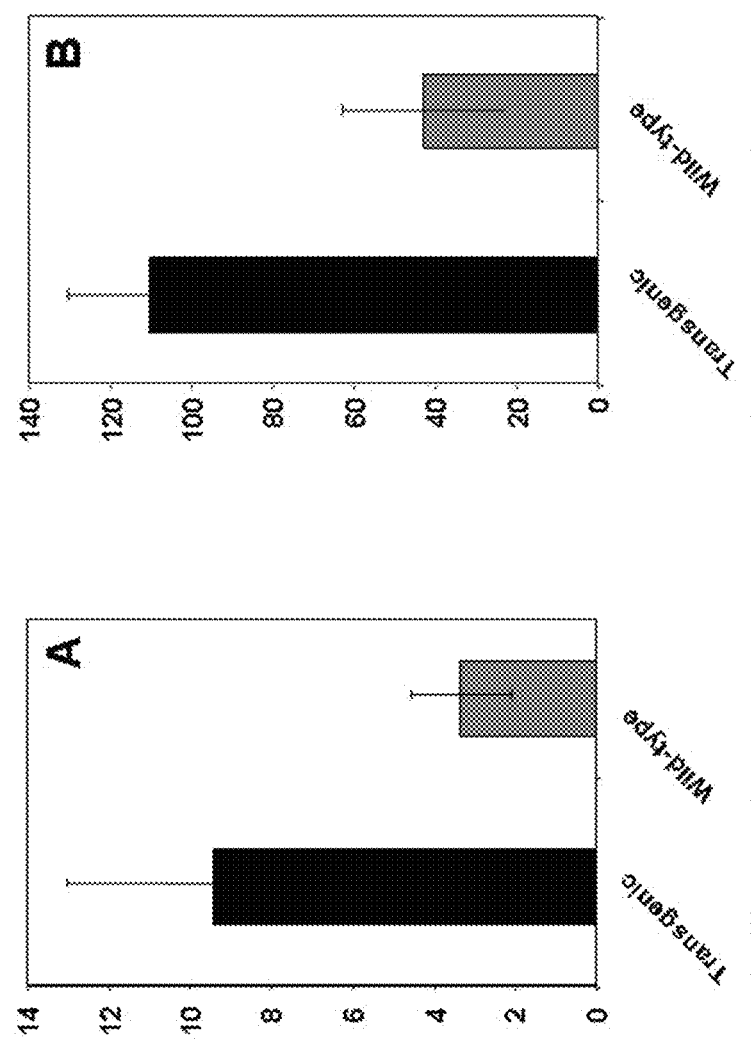
FIG. 8. Increase in bolt number (A) and silique number (B) in transgenic *Arabidopsis* over-expressing AT-AP2. The average bolt number from twelve T1 generation transgenic *Arabidopsis* lines and six non-transgenic wild-type control plants are presented in panel A. The silique number from a transgenic line over-expressing AT-AP2 (four plants) and a non-transgenic line (seven plants) are shown in panel B.

Transgenic *Arabidopsis* over-expressing the AT-AP2 gene, either under the control of the constitutive SCP1 promoter or the constitutive AT-UBQ10 promoter had greater number of siliques (pods) and branches (FIGS. 7 and 8).

Example 2

Vector Construction

The full length *Arabidopsis* AP2 gene was amplified from cDNA or genomic DNA with primers designed to introduce RcaI and SfuI sites to facilitate cloning. The PCR amplification product was sequenced and introduced into a plant expression vector containing the SCP Promoter and the PINII terminator. This entry vector was subsequently cloned into a plant transformation vector using Gateway multisite cloning (Invitrogen), introduced into *Agrobacterium tumafaciens* by electroporation and transformed into *Arabidopsis* by the floral dip method of Clough and Bent (Clough and Bent, (1998) *Floral dip: a simplified method for agrobacterium-mediated transformation of arabidopsis thaliana*, Plant Journal 16(6): 735-743.

The full length Soybean AP2 gene was isolated by screening DuPont EST libraries using the BlastX algorithm and the *Arabidopsis* AP2 sequence as template. The full-length soybean AP2 was amplified from this EST using primers that introduced NcoI and SfuI restriction enzyme sites to facilitate cloning. The full-length soybean AP2 was cloned into vectors under the control of the SCP1 and AT-UBQ10 promoters for constitutive expression in soybean.

Example 3

Rice Transformation Method

High-velocity ballistic bombardment using metal particles coated with the nucleic acid constructs was used to transform wild-type rice (Klein, et al., (1987) *Nature* 327:70-73; U.S. Pat. No. 4,945,050, incorporated by reference herein). A Biolistic PDS-1000/He (BioRAD Laboratories, Hercules, Calif.) was used for these complementation experiments. The particle bombardment technique was used to transform wild-type rice with the pGOS2::ZM-AP2 transcription factor. The bacterial hygromycin B phosphotransferase (Hpt II) gene from *Streptomyces hygroscopicus* (which confers resistance to the antibiotic) was used as the selectable marker for rice transformation. In the vector, pML18, the Hpt II gene was engineered with the 35S promoter from Cauliflower Mosaic Virus and the termination and polyadenylation signals from the octopine synthase gene of *Agrobacterium tumefaciens*. pML18 is described in WO 97/47731, the disclosure of which is hereby incorporated by reference.

Embryogenic callus cultures derived from the scutellum of germinating rice seeds served as source material for transformation experiments. This material is generated by germinating sterile rice seeds on a callus initiation media (MS salts, Nitsch and Nitsch vitamins, 1.0 mg/l 2,4-D and 10 μM $AgNO_3$) in the dark at 27-28° C. Embryogenic callus proliferating from the scutellum of the embryos is then transferred to CM media (N6 salts, Nitsch and Nitsch vitamins, 1 mg/l 2,4-D; Chu, et al., (1985) *Sci. Sinica* 18:659-668). Callus cultures are maintained on CM by routine sub-culture at two week intervals and used for transformation within 10 weeks of initiation. Callus is prepared for transformation by subculturing 0.5-1.0 mm pieces approximately 1 mm apart, arranged in a circular area of about 4 cm in diameter, in the center of a circle of Whatman® #541 paper placed on CM media. The plates with callus are incubated in the dark at 27-28° C. for 3-5 days. Prior to bombardment, the filters with callus are transferred to CM supplemented with 0.25 M mannitol and 0.25 M sorbitol for 3 hr in the dark. The petri dish lids are then left ajar for 20-45 minutes in a sterile hood to allow moisture on tissue to dissipate.

Each DNA fragment was co-precipitated with pML18 containing the selectable marker for rice transformation onto the surface of gold particles. To accomplish this, a total of 10 μg of DNA at a 2:1 ratio of trait:selectable marker DNAs were added to a 50 μl aliquot of gold particles that had been resuspended at a concentration of 60 mg ml$^{-1}$. Calcium chloride (50 μl of a 2.5 M solution) and spermidine (20 μl of a 0.1 M solution) were then added to the gold-DNA suspension as the tube was vortexing for 3 min. The gold particles were centrifuged in a microfuge for 1 second and the supernatant removed. The gold particles were then washed twice with 1 ml of absolute ethanol and resuspended in 50 μl of absolute ethanol and sonicated (bath sonicator) for one second to disperse the gold particles. The gold suspension was incubated at −70° C. for five minutes and sonicated (bath sonicator) to disperse the particles. Six μl of the DNA-coated gold particles was then loaded onto mylar macrocarrier disks and the ethanol was allowed to evaporate.

At the end of the drying period, a petri dish containing the tissue was placed in the chamber of the PDS-1000/He. The air in the chamber was then evacuated to a vacuum of 28-29 inches Hg. The macrocarrier was accelerated with a helium shock wave using a rupture membrane that bursts when the He pressure in the shock tube reaches 1080-1100 psi. The tissue was placed approximately 8 cm from the stopping screen and the callus was bombarded two times. Two to four plates of tissue were bombarded in this way with the DNA-coated gold particles. Following bombardment, the callus tissue was transferred to CM media without supplemental sorbitol or mannitol.

Three to five days after bombardment, the callus tissue was transferred to SM media (CM medium containing 50 mg/l hygromycin). To accomplish this, callus tissue was transferred from plates to sterile 50 ml conical tubes and weighed. Molten top-agar at 40° C. was added using 2.5 ml of top agar/100 mg of callus. Callus clumps were broken into fragments of less than 2 mm diameter by repeated dispensing through a 10 ml pipette. Three ml aliquots of the callus suspension were plated onto fresh SM media and the plates were incubated in the dark for 4 weeks at 27-28° C. After 4 weeks, transgenic callus events were identified, transferred to fresh SM plates and grown for an additional 2 weeks in the dark at 27-28° C.

Growing callus was transferred to RM1 media (MS salts, Nitsch and Nitsch vitamins, 2% sucrose, 3% sorbitol, 0.4% Gelrite®+50 ppm hyg B) for 2 weeks in the dark at 25° C. After 2 weeks the callus was transferred to RM2 media (MS salts, Nitsch and Nitsch vitamins, 3% sucrose, 0.4% Gelrite®+50 ppm hyg B) and placed under cool white light (40 $\mu Em^{-2}s^{-1}$) with a 12 hr photoperiod at 25° C. and 30-40% humidity. After 2-4 weeks in the light, callus began to organize and form shoots. Shoots were removed from surrounding callus/media and gently transferred to RM3 media (½×MS salts, Nitsch and Nitsch vitamins, 1% sucrose+50 ppm hygromycin B) in Phytatrays™ (Sigma Chemical Co., St. Louis, Mo.) and incubation was continued using the same conditions as described in the previous step. The resultant T0 transformants were transferred from RM3 to 4" pots containing Metro mix@ 350 after 2-3 weeks, when sufficient root and shoot growth had occurred.

Example 4

Expression of AP2 Transcription Factor in Soybean

The *Arabidospis* AP2 gene and the soy AP2 gene in plant transformation vectors under the control of constitutive plant promoters (AT-UBQ10 and SCP PRO) were transformed into soybean using biolistic methods. Over-expression of the *Arabidopsis* AP2 gene or soy AP2 gene in soybean is expected to increase flower or pod number, branch number or increase the retention of soybean flowers or pods. An increase in one or more of these components is expected to increase yield in soybean.

Example 5

Overexpression of AP2 Transcription Factor Sequences in Maize

Immature maize embryos from greenhouse donor plants are bombarded with a plasmid containing an AP2 transcription factor sequence (such as Zm-AP2 transcription factor/SEQ ID NO: 1) under the control of the UBI promoter and the selectable marker gene PAT (Wohlleben, et al., (1988) *Gene* 70:25-37), which confers resistance to the herbicide Bialaphos. Alternatively, the selectable marker gene is provided on a separate plasmid. Transformation is performed as follows. Media recipes follow below.

Preparation of Target Tissue

The ears are husked and surface sterilized in 30% Clorox@ bleach plus 0.5% Micro detergent for 20 minutes, and rinsed two times with sterile water. The immature embryos are excised and placed embryo axis side down (scutellum side up), 25 embryos per plate, on 560Y medium for 4 hours and then aligned within the 2.5 cm target zone in preparation for bombardment.

A plasmid vector comprising the AP2 transcription factor sequence operably linked to a ubiquitin promoter is made. This plasmid DNA plus plasmid DNA containing a PAT selectable marker is precipitated onto 1.1 µm (average diameter) tungsten pellets using a $CaCl_2$ precipitation procedure as follows: 100 µl prepared tungsten particles in water; 10 µl (1 µg) DNA in Tris EDTA buffer (1 µg total DNA); 100 µl 2.5 M $CaCl_2$; and, 10 µl 0.1 M spermidine. Each reagent is added sequentially to the tungsten particle suspension, while maintained on the multitube vortexer. The final mixture is sonicated briefly and allowed to incubate under constant vortexing for 10 minutes. After the precipitation period, the tubes are centrifuged briefly, liquid removed, washed with 500 ml 100% ethanol, and centrifuged for 30 seconds. Again the liquid is removed, and 105 µl 100% ethanol is added to the final tungsten particle pellet. For particle gun bombardment, the tungsten/DNA particles are briefly sonicated and 10 µl spotted onto the center of each macrocarrier and allowed to dry about 2 minutes before bombardment.

The sample plates are bombarded at level #4 in particle gun (U.S. Pat. No. 5,240,855). All samples receive a single shot at 650 PSI, with a total of ten aliquots taken from each tube of prepared particles/DNA.

Following bombardment, the embryos are kept on 560Y medium for 2 days, then transferred to 560R selection medium containing 3 mg/liter Bialaphos, and subcultured every 2 weeks. After approximately 10 weeks of selection, selection-resistant callus clones are transferred to 288J medium to initiate plant regeneration. Following somatic embryo maturation (2-4 weeks), well-developed somatic embryos are transferred to medium for germination and transferred to the lighted culture room. Approximately 7-10 days later, developing plantlets are transferred to 272V hormone-free medium in tubes for 7-10 days until plantlets are well established. Plants are then transferred to inserts in flats (equivalent to 2.5" pot) containing potting soil and grown for 1 week in a growth chamber, subsequently grown an additional 1-2 weeks in the greenhouse, then transferred to classic 600 pots (1.6 gallon) and grown to maturity. Plants are monitored and scored for an increase in nitrogen use efficiency, increase yield, or an increase in stress tolerance.

Bombardment medium (560Y) comprises 4.0 g/l N6 basal salts (SIGMA C-1416), 1.0 ml/l Eriksson's Vitamin Mix (1000× SIGMA-1511), 0.5 mg/l thiamine HCl, 120.0 g/l sucrose, 1.0 mg/l 2,4-D, and 2.88 g/l L-proline (brought to volume with D-I $H_2O$ following adjustment to pH 5.8 with KOH); 2.0 g/l Gelrite® (added after bringing to volume with D-I $H_2O$); and 8.5 mg/l silver nitrate (added after sterilizing the medium and cooling to room temperature). Selection medium (560R) comprises 4.0 g/l N6 basal salts (SIGMA C-1416), 1.0 ml/l Eriksson's Vitamin Mix (1000X SIGMA-1511), 0.5 mg/l thiamine HCl, 30.0 g/l sucrose, and 2.0 mg/l 2,4-D (brought to volume with D-I $H_2O$ following adjustment to pH 5.8 with KOH); 3.0 g/l Gelrite® (added after bringing to volume with D-I $H_2O$); and 0.85 mg/l silver nitrate and 3.0 mg/l bialaphos (both added after sterilizing the medium and cooling to room temperature).

Plant regeneration medium (288J) comprises 4.3 g/l MS salts (GIBCO 11117-074), 5.0 ml/l MS vitamins stock solution (0.100 g nicotinic acid, 0.02 g/l thiamine HCL, 0.10 g/l pyridoxine HCL, and 0.40 g/l glycine brought to volume with polished D-I $H_2O$) (Murashige and Skoog, (1962) *Physiol. Plant.* 15:473), 100 mg/l myo-inositol, 0.5 mg/l zeatin, 60 g/l sucrose, and 1.0 ml/l of 0.1 mM abscisic acid (brought to volume with polished D-I $H_2O$ after adjusting to pH 5.6); 3.0 g/l Gelrite® (added after bringing to volume with D-I $H_2O$); and 1.0 mg/l indoleacetic acid and 3.0 mg/l bialaphos (added after sterilizing the medium and cooling to 60° C.). Hormone-free medium (272V) comprises 4.3 g/l MS salts (GIBCO 11117-074), 5.0 ml/l MS vitamins stock solution (0.100 g/l nicotinic acid, 0.02 g/l thiamine HCL, 0.10 g/l pyridoxine HCL, and 0.40 g/l glycine brought to volume with polished D-I $H_2O$), 0.1 g/l myo-inositol, and 40.0 g/l sucrose (brought to volume with polished D-I $H_2O$ after adjusting pH to 5.6); and 6 g/l Bacto™-agar (added after bringing to volume with polished D-I $H_2O$), sterilized and cooled to 60° C.

Example 6

*Agrobacterium*-Mediated Transformation

For *Agrobacterium*-mediated transformation of maize with an AP2 transcription factor polynucleotide the method of Zhao is employed (U.S. Pat. No. 5,981,840, and PCT Patent Publication Number WO98/32326; the contents of which are hereby incorporated by reference). Briefly, immature embryos are isolated from maize and the embryos contacted with a suspension of *Agrobacterium,* where the bacteria are capable of transferring the AP2 transcription factor polynucleotide to at least one cell of at least one of the immature embryos (step 1: the infection step). In this step the immature embryos are immersed in an *Agrobacterium* suspension for the initiation of inoculation. The embryos are co-cultured for a time with the *Agrobacterium* (step 2: the co-cultivation step). The immature embryos are cultured on solid medium following the infection step. Following this co-cultivation period an optional "resting" step is contemplated. In this resting step, the embryos are incubated in the presence of at least one antibiotic known to inhibit the growth of *Agrobacterium* without the addition of a selective agent for plant transformants (step 3: resting step). The immature embryos are cultured on solid medium with antibiotic, but without a selecting agent, for elimination of *Agrobacterium* and for a resting phase for the infected cells. Next, inoculated embryos are cultured on medium containing a selective agent and growing transformed callus is recovered (step 4: the selection step). The immature embryos are cultured on solid medium with a selective agent resulting in the selective growth of transformed cells. The callus is then regenerated into plants (step 5: the regeneration step), and calli grown on selective medium are cultured on solid medium to regenerate the plants.

Example 7

Soybean Embryo Transformation

Culture Conditions

Soybean embryogenic suspension cultures (cv. Jack) are maintained in 35 ml liquid medium SB196 (see recipes below) on rotary shaker, 150 rpm, 26° C. with cool white fluorescent lights on 16:8 hr day/night photoperiod at light intensity of 60-85 µE/m2/s. Cultures are subcultured every 7 days to two weeks by inoculating approximately 35 mg of tissue into 35 ml of fresh liquid SB196 (the preferred subculture interval is every 7 days).

Soybean embryogenic suspension cultures are transformed with the plasmids and DNA fragments described in the following examples by the method of particle gun bombardment (Klein, et al., (1987) *Nature* 327:70).

Soybean Embryogenic Suspension Culture Initiation

Soybean cultures are initiated twice each month with 5-7 days between each initiation. Pods with immature seeds from available soybean plants 45-55 days after planting are picked, removed from their shells and placed into a sterilized magenta box. The soybean seeds are sterilized by shaking them for 15 minutes in a 5% Clorox® solution with 1 drop of ivory soap (95 ml of autoclaved distilled water plus 5 ml Clorox® and 1 drop of soap). Mix well. Seeds are rinsed using 2 1-liter bottles of sterile distilled water and those less than 4 mm are placed on individual microscope slides. The small end of the seed are cut and the cotyledons pressed out of the seed coat. Cotyledons are transferred to plates containing SB1 medium (25-30 cotyledons per plate). Plates are wrapped with fiber tape and stored for 8 weeks. After this time secondary embryos are cut and placed into SB196 liquid media for 7 days.

Preparation of DNA for Bombardment

Either an intact plasmid or a DNA plasmid fragment containing the genes of interest and the selectable marker gene are used for bombardment. Plasmid DNA for bombardment are routinely prepared and purified using the method described in the Promega™ Protocols and Applications Guide, Second Edition (page 106). Fragments of the plasmids carrying an AP2 transcription factor polynucleotide are obtained by gel isolation of double digested plasmids. In each case, 100 µg of plasmid DNA is digested in 0.5 ml of the specific enzyme mix that is appropriate for the plasmid of interest. The resulting DNA fragments are separated by gel electrophoresis on 1% SeaPlaque GTG agarose (BioWhitaker Molecular Applications) and the DNA fragments containing the AP2 transcription factor polynucleotide are cut from the agarose gel. DNA is purified from the agarose using the GELase digesting enzyme following the manufacturer's protocol.

A 50 µl aliquot of sterile distilled water containing 3 mg of gold particles (3 mg gold) is added to 5 µl of a 1 µg/µl DNA solution (either intact plasmid or DNA fragment prepared as described above), 50 µl 2.5M $CaCl_2$ and 20 µl of 0.1 M spermidine. The mixture is shaken 3 min on level 3 of a vortex shaker and spun for 10 sec in a bench microfuge. After a wash with 400 µl 100% ethanol the pellet is suspended by sonication in 40 µl of 100% ethanol. Five µl of DNA suspension is dispensed to each flying disk of the Biolistic PDS1000/HE instrument disk. Each 5 µl aliquot contains approximately 0.375 mg gold per bombardment (i.e., per disk).

Tissue Preparation and Bombardment with DNA

Approximately 150-200 mg of 7 day old embryonic suspension cultures are placed in an empty, sterile 60×15 mm petri dish and the dish covered with plastic mesh. Tissue is bombarded 1 or 2 shots per plate with membrane rupture pressure set at 1100 PSI and the chamber evacuated to a vacuum of 27-28 inches of mercury. Tissue is placed approximately 3.5 inches from the retaining/stopping screen.

Selection of Transformed Embryos

Transformed embryos were selected either using hygromycin (when the hygromycin phosphotransferase, HPT, gene was used as the selectable marker) or chlorsulfuron (when the acetolactate synthase, ALS, gene was used as the selectable marker).

Hygromycin (HPT) Selection

Following bombardment, the tissue is placed into fresh SB196 media and cultured as described above. Six days post-bombardment, the SB196 is exchanged with fresh SB196 containing a selection agent of 30 mg/L hygromycin. The selection media is refreshed weekly. Four to six weeks post selection, green, transformed tissue may be observed growing from untransformed, necrotic embryogenic clusters. Isolated, green tissue is removed and inoculated into multiwell plates to generate new, clonally propagated, transformed embryogenic suspension cultures.

Chlorsulfuron (ALS) Selection

Following bombardment, the tissue is divided between 2 flasks with fresh SB196 media and cultured as described above. Six to seven days post-bombardment, the SB196 is exchanged with fresh SB196 containing selection agent of 100 ng/ml Chlorsulfuron. The selection media is refreshed weekly. Four to six weeks post selection, green, transformed tissue may be observed growing from untransformed, necrotic embryogenic clusters. Isolated, green tissue is removed and inoculated into multiwell plates containing SB196 to generate new, clonally propagated, transformed embryogenic suspension cultures.

Regeneration of Soybean Somatic Embryos into Plants

In order to obtain whole plants from embryogenic suspension cultures, the tissue must be regenerated.

Embryo Maturation

Embryos are cultured for 4-6 weeks at 26° C. in SB196 under cool white fluorescent (Phillips cool white Econowatt F40/CW/RS/EW) and Agro (Phillips F40 Agro) bulbs (40 watt) on a 16:8 hr photoperiod with light intensity of 90-120 uE/m2s. After this time embryo clusters are removed to a solid agar media, SB166, for 1-2 weeks. Clusters are then subcultured to medium SB103 for 3 weeks. During this period, individual embryos can be removed from the clusters and screened for levels of AP2 transcription factor expression and/or activity.

Embryo Desiccation and Germination

Matured individual embryos are desiccated by placing them into an empty, small petri dish (35×10 mm) for approximately 4-7 days. The plates are sealed with fiber tape (creating a small humidity chamber). Desiccated embryos are planted into SB71-4 medium where they were left to germinate under the same culture conditions described above. Germinated plantlets are removed from germination medium and rinsed thoroughly with water and then planted in Redi-Earth in 24-cell pack tray, covered with clear plastic dome. After 2 weeks the dome is removed and plants hardened off for a further week. If plantlets looked hardy they are transplanted to 10" pot of Redi-Earth with up to 3 plantlets per pot. After 10 to 16 weeks, mature seeds are harvested, chipped and analyzed for proteins.

Media Recipes
SB 196 - FN Lite liquid proliferation medium (per liter) -

| | |
|---|---|
| MS FeEDTA - 100x Stock 1 | 10 ml |
| MS Sulfate - 100x Stock 2 | 10 ml |
| FN Lite Halides - 100x Stock 3 | 10 ml |
| FN Lite P, B, Mo - 100x Stock 4 | 10 ml |
| B5 vitamins (1 ml/L) | 1.0 ml |
| 2,4-D (10 mg/L final concentration) | 1.0 ml |
| $KNO_3$ | 2.83 gm |
| $(NH_4)_2SO_4$ | 0.463 gm |
| Asparagine | 1.0 gm |
| Sucrose (1%) | 10 gm |
| pH | 5.8 |

FN Lite Stock Solutions

| Stock # | | 1000 ml | 500 ml |
|---|---|---|---|
| 1 | MS Fe EDTA 100x Stock | | |
| | $Na_2$ EDTA* | 3.724 g | 1.862 g |
| | $FeSO_4$—$7H_2O$ | 2.784 g | 1.392 g |
| 2 | MS Sulfate 100x stock | | |
| | $MgSO_4$—$7H_2O$ | 37.0 g | 18.5 g |
| | $MnSO_4$—$H_2O$ | 1.69 g | 0.845 g |
| | $ZnSO_4$—$7H_2O$ | 0.86 g | 0.43 g |
| | $CuSO_4$—$5H_2O$ | 0.0025 g | 0.00125 g |
| 3 | FN Lite Halides 100x Stock | | |
| | $CaCl_2$—$2H_2O$ | 30.0 g | 15.0 g |
| | KI | 0.083 g | 0.0715 g |
| | $CoCl_2$—$6H_2O$ | 0.0025 g | 0.00125 g |
| 4 | FN Lite P, B, Mo 100x Stock | | |
| | $KH_2PO_4$ | 18.5 g | 9.25 g |
| | $H_3BO_3$ | 0.62 g | 0.31 g |
| | $Na_2MoO_4$—$2H_2O$ | 0.025 g | 0.0125 g |

*Add first, dissolve in dark bottle while stirring

SB1 solid medium (per liter) comprises: 1 pkg. MS salts (GIBCO/BRL—Cat #11117-066); 1 ml B5 vitamins 1000× stock; 31.5 g sucrose; 2 ml 2,4-D (20 mg/L final concentration); pH 5.7; and, 8 g TC agar.

SB 166 solid medium (per liter) comprises: 1 pkg. MS salts (GIBCO/BRL—Cat #11117-066); 1 ml B5 vitamins 1000× stock; 60 g maltose; 750 mg $MgCl_2$ hexahydrate; 5 g activated charcoal; pH 5.7; and, 2 g Gelrite®.

SB 103 solid medium (per liter) comprises: 1 pkg. MS salts (GIBCO/BRL—Cat #11117-066); 1 ml B5 vitamins 1000× stock; 60 g maltose; 750 mg MgCl2 hexahydrate; pH 5.7; and, 2 g Gelrite®.

SB 71-4 solid medium (per liter) comprises: 1 bottle Gamborg's B5 salts w/sucrose (GIBCO/BRL—Cat #21153-036); pH 5.7; and, 5 g TC agar.

2,4-D stock is obtained premade from Phytotech cat #D 295—concentration is 1 mg/ml.

B5 Vitamins Stock (per 100 ml) which is stored in aliquots at −20° C. comprises: 10 g myo-inositol; 100 mg nicotinic acid; 100 mg pyridoxine HCl; and, 1 g thiamine. If the solution does not dissolve quickly enough, apply a low level of heat via the hot stir plate.

Chlorsulfuron Stock comprises: 1 mg/ml in 0.01 N Ammonium Hydroxide.

Example 8

Variants of AP2 Transcription Factor

A. Variant Nucleotide Sequences of AP2 Transcription Factor That Do Not Alter the Encoded Amino Acid Sequence The AP2 nucleotide sequences set forth in SEQ ID NOS: 1 and 3 are used to generate variant nucleotide sequences having the nucleotide sequence of the open reading frame with about 70%, 75%, 80%, 85%, 90% or 95% nucleotide sequence identity when compared to the corresponding starting unaltered ORF nucleotide sequence. These functional variants are generated using a standard codon table. While the nucleotide sequence of the variant is altered, the amino acid sequence encoded by the open reading frame does not change.

B. Variant Amino Acid Sequences of AP2 Transcription Factor

Variant amino acid sequences of AP2 are generated. In this example, one or more amino acids are altered. Specifically, the open reading frame set forth in SEQ ID NOS: 2 or 4 are reviewed to determine the appropriate amino acid alteration. The selection of an amino acid to change is made by consulting a protein alignment with orthologs and other gene family members from various species. See, FIGS. 1 and 2. An amino acid is selected that is deemed not to be under high selection pressure (not highly conserved) and which is rather easily substituted by an amino acid with similar chemical characteristics (i.e., similar functional side-chain). Assays as outlined elsewhere herein may be followed to confirm functionality. Variants having about 70%, 75%, 80%, 85%, 90% or 95% nucleic acid sequence identity to each of SEQ ID NOS: 1 or 3 are generated using this method.

C. Additional Variant Amino Acid Sequences of AP2 Transcription Factor.

In this example, artificial protein sequences are created having 80%, 85%, 90% and 95% identity relative to the reference protein sequence. This latter effort requires identifying conserved and variable regions from the alignment set forth in FIGS. 1 and 2 and then the judicious application of an amino acid substitutions table. These parts will be discussed in more detail below.

Largely, the determination of which amino acid sequences are altered is made based on the conserved regions among the AP2 transcription factor proteins or among the other AP2 transcription factor polypeptides. See, FIGS. 1 and 2. Based on the sequence alignment, the various regions of the polypeptides that can likely be altered can be determined. It is recognized that conservative substitutions can be made in the conserved regions without altering function. In addition, one of skill will understand that functional variants of the AP2 transcription factor sequence of the invention can have minor non-conserved amino acid alterations in the conserved domain.

Artificial protein sequences are then created that are different from the original in the intervals of 80-85%, 85-90%, 90-95% and 95-100% identity. Midpoints of these intervals are targeted, with liberal latitude of plus or minus 1%, for example. The amino acids substitutions will be effected by a custom Perl script. The substitution table is provided below in Table 1.

First, any conserved amino acids in the protein that should not be changed are identified and "marked off" for insulation from the substitution. The start methionine will of course be added to this list automatically. Next, the changes are made.

H, C and P are not changed. The changes will occur with isoleucine first, sweeping N-terminal to C-terminal. Then leucine, and so on down the list until the desired target is reached. Interim number substitutions can be made so as not to cause reversal of changes. The list is ordered 1-17, so start with as many isoleucine changes as needed before leucine, and so on down to methionine. Clearly many amino acids will in this manner not need to be changed. L, I and V will involve a 50:50 substitution of the two alternate optimal substitutions.

The variant amino acid sequences are written as output. Perl script is used to calculate the percent identities. Using this procedure, variants of AP2 transcription factor are generated having about 82%, 87%, 92% and 97% amino acid identity to the starting unaltered ORF nucleotide sequence of SEQ ID NOS: 1 or 3.

TABLE 1

Substitution Table

| Amino Acid | Strongly Similar and Optimal Substitution | Rank of Order to Change | Comment |
|---|---|---|---|
| I | L, V | 1 | 50:50 substitution |
| L | I, V | 2 | 50:50 substitution |
| V | I, L | 3 | 50:50 substitution |
| A | G | 4 | |
| G | A | 5 | |
| D | E | 6 | |
| E | D | 7 | |
| W | Y | 8 | |
| Y | W | 9 | |
| S | T | 10 | |
| T | S | 11 | |
| K | R | 12 | |
| R | K | 13 | |
| N | Q | 14 | |
| Q | N | 15 | |
| F | Y | 16 | |
| M | L | 17 | First methionine cannot change |
| H | | Na | No good substitutes |
| C | | Na | No good substitutes |
| P | | Na | No good substitutes |

The article "a" and "an" are used herein to refer to one or more than one (i.e., to at least one) of the grammatical object of the article. By way of example, "an element" means one or more element.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, certain changes and modifications may be practiced within the scope of the appended claims.

That which is claimed:

1. An isolated polynucleotide encoding a polypeptide having AP2 transcription factor activity and comprising a nucleotide sequence selected from the group consisting of:
   (a) the nucleotide sequence set forth in SEQ ID NO: 3; and
   (b) a nucleotide sequence encoding the amino acid sequence of SEQ ID NO: 4
   wherein said nucleotide sequence is operably linked to a heterologous promoter.

2. An expression cassette comprising the polynucleotide of claim 1.

3. The expression cassette of claim 2, wherein said polynucleotide is operably linked to a promoter that drives expression in a plant.

4. The expression cassette of claim 3, wherein said polynucleotide is operably linked to a constitutive promoter.

5. A transgenic plant comprising the expression cassette of claim 3 or claim 4.

6. The transgenic plant of claim 5, wherein said plant is maize, wheat, rice, barley, sorghum, rye, soybean, brassica, or sunflower.

7. A transgenic plant comprising a polynucleotide operably linked to a promoter that drives expression in the plant, wherein said polynucleotide comprises a nucleotide sequence of claim 1, and wherein the AP2 transcription factor level in said plant is modulated relative to a control plant.

8. The plant of claim 5, wherein said plant has an increased level of the polypeptide of SEQ ID NO: 4.

9. The plant of claim 5, wherein said plant has a phenotype selected from the group consisting of:
   (a) an increased total seed number;
   (b) an increased total seed weight;
   (c) an increased harvest index; and
   (d) an increased biomass
   as compared to a non-transformed control plant.

10. A method of increasing the level of a polypeptide in a plant comprising introducing into said plant the expression cassette of claim 3 or claim 4.

11. The method of claim 10, wherein the yield of the plant is increased as compared to a non-transformed plant.

12. The method of claim 10, wherein increasing the level of said polypeptide produces a phenotype in the plant selected from the group consisting of:
   (a) an increased total seed number;
   (b) an increased total seed weight;
   (c) an increased harvest index; and
   (d) an increased biomass
   as compared to a non-transformed control plant.

13. The method of claim 11, wherein said expression cassette is stably integrated into the genome of the plant.

14. The method of claim 13, wherein said plant is maize, wheat, rice, barley, sorghum, rye, soybean, brassica or sunflower.

15. A method of increasing yield in a plant comprising increasing expression of an AP2 transcription factor polypeptide in said plant, wherein said AP2 transcription factor polypeptide has AP2 transcription factor protein activity and is:
   a polypeptide comprising the amino acid sequence SEQ ID NO: 4.

16. The method of claim 15, comprising introducing into said plant an expression cassette comprising a polynucleotide encoding said AP2 transcription factor polypeptide operably linked to a promoter that drives expression in a plant cell, wherein said polynucleotide comprises a nucleotide sequence of:
   (a) the nucleotide sequence of SEQ ID NO: 3; and
   (b) a nucleotide sequence encoding the polypeptide of SEQ ID NO: 4.

17. The method of claim 16, comprising:
   (a) transforming a plant cell with said expression cassette; and
   (b) regenerating a transformed plant from the transformed plant cell of step (a).

18. The method of claim 16, wherein said expression cassette is stably incorporated into the genome of the plant.

19. The method of claim 16, wherein said promoter is a constitutive promoter.

* * * * *

SEQUENCE LISTING

<160> NUMBER OF SEQ ID NOS: 16

<210> SEQ ID NO 1
<211> LENGTH: 919
<212> TYPE: DNA
<213> ORGANISM: Arabidopsis thaliana

<400> SEQUENCE: 1
cttcaatcta atttcttctc cttatcatcc tcttgttctt gatgttcaac gatgccataa 60
agaaaaactg aacaacccta aagtactgta taaatcctat atcaaatttt ttttttggaa 120
gaaaaggcta tatttaaaag aaaatcaagc aaaagtagat cctcggatgt atgggaagag 180
gccttttgga ggtgatgaat ctgaagaaag ggaagaagat gagaacttgt tcccggtctt 240
ctcggcccga tctcaacacg acatgcgtgt tatggtctcg gccttgactc aagtaatcgg 300
aaaccaacaa agcaaatctc atgataacat cagctctatt gatgataact atccttctgt 360
gtataatcca caagacccta atcaacaagt tgcgcctact catcaagacc aaggggactt 420
gaggaggaga cattatagag gtgtaaggca aaggccatgg ggaaagtggg cagctgaaat 480
ccgagaccca aaaaaggcgg cacgtgtgtg gctcgggaca tttgaaaccg ctgaatctgc 540
ggccttagct tatgatgaag cagccctaaa gttcaaagga agcaaagcaa aactcaattt 600
cccggagagg gttcagcttg gaagtaactc tacatattac tcctccaacc aaattccaca 660
aatggaacca caaagtatac cgaactataa tcaatactat catgatgcga gtagtggtga 720
tatgctaagt tttaatttgg gcggtgggta tgggagtggt accggatatt caatgtctca 780

```
tgataatagt actacgactg ctgctacaac ttcttcgtct ctggtggct cttctaggca        840 acaagaagag caagattatg ccagattctg gcgctttggg gattcttctt cctctcctca        900
ttcgggatat taattcgaa                                                      919
```

<210> SEQ ID NO 2
<211> LENGTH: 248
<212> TYPE: PRT
<213> ORGANISM: Arabidopsis thaliana

<400> SEQUENCE: 2

```
Met Tyr Gly Lys Arg Pro Phe Gly Gly Asp Glu Ser Glu Arg Glu
 1               5                  10                  15

Glu Asp Glu Asn Leu Phe Pro Val Phe Ser Ala Arg Ser Gln His Asp
                20                  25                  30

Met Arg Val Met Val Ser Ala Leu Thr Gln Val Ile Gly Asn Gln Gln
                35                  40                  45

Ser Lys Ser His Asp Asn Ile Ser Ser Ile Asp Asp Asn Tyr Pro Ser
    50                  55                  60

Val Tyr Asn Pro Gln Asp Pro Asn Gln Gln Val Ala Pro Thr His Gln
65                  70                  75                  80

Asp Gln Gly Asp Leu Arg Arg Arg His Tyr Arg Gly Val Arg Gln Arg
                85                  90                  95

Pro Trp Gly Lys Trp Ala Ala Glu Ile Arg Asp Pro Lys Lys Ala Ala
                100                 105                 110

Arg Val Trp Leu Gly Thr Phe Glu Thr Ala Glu Ser Ala Ala Leu Ala
                115                 120                 125

Tyr Asp Glu Ala Ala Leu Lys Phe Lys Gly Ser Lys Ala Lys Leu Asn
                130                 135                 140

Phe Pro Glu Arg Val Gln Leu Gly Ser Asn Ser Thr Tyr Tyr Ser Ser
145                 150                 155                 160

Asn Gln Ile Pro Gln Met Glu Pro Gln Ser Ile Pro Asn Tyr Asn Gln
                165                 170                 175

Tyr Tyr His Asp Ala Ser Ser Gly Asp Met Leu Ser Phe Asn Leu Gly
                180                 185                 190

Gly Gly Tyr Gly Ser Gly Thr Gly Tyr Ser Met Ser His Asp Asn Ser
                195                 200                 205

Thr Thr Thr Ala Ala Thr Thr Ser Ser Ser Ser Gly Gly Ser Ser Arg
                210                 215                 220

Gln Gln Glu Glu Gln Asp Tyr Ala Arg Phe Trp Arg Phe Gly Asp Ser
225                 230                 235                 240

Ser Ser Ser Pro His Ser Gly Tyr
                245
```

<210> SEQ ID NO 3
<211> LENGTH: 1217
<212> TYPE: DNA
<213> ORGANISM: Glycine max

<400> SEQUENCE: 3

```
cggtttcagt atttatcatc aaatcactgg ttctcctttt atagaaatct tagatctgct         60
tttaacacaa ggttttggtg gagaagaaga agcaaagagg gtgtataaat agaagagtag        120
aagaagcagc aattgagggg aaagttagtg agcaaggtgg atcgaaggca agggaagagg        180
tctctccctc ctcatgagga gaaaaagaa gctttcaact ttcctattat tcatctaaca        240
ccatctcaaa atcgaaagga acaagcttca ccatcatcac cacccttttc actcctcatg        300
```

```
agtaccaacc aaaacaccac cttcttcccc ctcccacatg gccaaataac tacttctgaa      360
tttgttaata gccagaacaa tccatcccag gctacaaatc aaggcattga tgatattagg      420
aaaaagcact atagaggagt taggcagaga ccatggggca atgggcagc agaaataaga       480 gaccctaaga aagcagctag agtgtggctt ggcacctttg acacggcaga ggctgcagct      540
atggcttatg atgctgctgc attgaggttc aaaggaaaca aagcaaagct caattttcct      600
gaacgtgttg ttatgccaat accatcacaa accaatacca attacaataa taacaatacc      660
acttcttcat catcagctcc tactacacaa ccttcttctc ttccaccacc accatcacaa      720
tctctacaaa atagtagcaa taataatagt tctctttcat cagaagggtt tccaaatctt      780
gaggagtatg caaggttgct gaattgtagc gatgatgatg actttcaacg tgttgcattg      840
gggctctacc agcatcacaa taatgaggat tatatttatg gttcatcaca accaccacca      900
gtgccgtttt ttgtgtcttc ttattcttct tcttctgcaa tggcatcttc attttctgat      960
tttcttggtc aaggagggag tggttttgat gaagagaaca agaggggggtc gtagtttttt    1020 tgtctctgaa ttctgagcac tgcatgctgg tggaaaagtg ggggctagct aggttgctgc     1080
cacaacaatt aaggaagttc aatcacacat ctcttatttg ttcttttgtt tttattattc     1140
caattacaaa ataatacctg aggtctaaat cagattataa tactcctcaa aaaaaaaaaa     1200
aaaaaaaaaa aaaaaaa                                                    1217

<210> SEQ ID NO 4
<211> LENGTH: 238
<212> TYPE: PRT
<213> ORGANISM: Glycine max

<400> SEQUENCE: 4

Met Ser Thr Asn Gln Asn Thr Thr Phe Phe Pro Leu Pro His Gly Gln
  1               5                  10                  15

Ile Thr Thr Ser Glu Phe Val Asn Ser Gln Asn Pro Ser Gln Ala
             20                  25                  30

Thr Asn Gln Gly Ile Asp Asp Ile Arg Lys Lys His Tyr Arg Gly Val
         35                  40                  45

Arg Gln Arg Pro Trp Gly Lys Trp Ala Ala Glu Ile Arg Asp Pro Lys
     50                  55                  60

Lys Ala Ala Arg Val Trp Leu Gly Thr Phe Asp Thr Ala Glu Ala Ala
 65                  70                  75                  80

Ala Met Ala Tyr Asp Ala Ala Ala Leu Arg Phe Lys Gly Asn Lys Ala
                 85                  90                  95

Lys Leu Asn Phe Pro Glu Arg Val Val Met Pro Ile Pro Ser Gln Thr
            100                 105                 110

Asn Thr Asn Tyr Asn Asn Asn Thr Thr Ser Ser Ser Ala Pro
        115                 120                 125

Thr Thr Gln Pro Ser Ser Leu Pro Pro Pro Ser Gln Ser Leu Gln
    130                 135                 140

Asn Ser Ser Asn Asn Asn Ser Ser Leu Ser Ser Glu Gly Phe Pro Asn
145                 150                 155                 160

Leu Glu Glu Tyr Ala Arg Leu Leu Asn Cys Ser Asp Asp Asp Phe
                165                 170                 175

Gln Arg Val Ala Leu Gly Leu Tyr Gln His His Asn Asn Glu Asp Tyr
            180                 185                 190

Ile Tyr Gly Ser Ser Gln Pro Pro Val Pro Phe Phe Val Ser Ser
        195                 200                 205
```

```
Tyr Ser Ser Ser Ala Met Ala Ser Ser Phe Ser Asp Phe Leu Gly
        210                 215                 220

Gln Gly Gly Ser Gly Phe Asp Glu Glu Asn Lys Arg Gly Ser
225                 230                 235

<210> SEQ ID NO 5
<211> LENGTH: 61
<212> TYPE: PRT
<213> ORGANISM: Artificial Sequence
<220> FEATURE:
<223> OTHER INFORMATION: Consensus AP2 domain
<221> NAME/KEY: VARIANT
<222> LOCATION: 35, 39, 42, 46, 50, 54
<223> OTHER INFORMATION: Xaa = Any Amino Acid
<221> NAME/KEY: VARIANT
<222> LOCATION: 35, 39, 42, 46, 50, 54
<223> OTHER INFORMATION: Xaa = Any Amino Acid
<221> NAME/KEY: VARIANT
<222> LOCATION: 35, 39, 42, 46, 50, 54
<223> OTHER INFORMATION: Xaa = Any Amino Acid

<400> SEQUENCE: 5

Arg Arg Arg His Tyr Arg Gly Val Arg Gln Arg Pro Trp Gly Lys Trp
1               5                   10                  15

Ala Ala Glu Ile Arg Asp Pro Lys Lys Ala Ala Arg Val Trp Leu Gly
            20                  25                  30

Thr Phe Xaa Thr Ala Glu Xaa Ala Ala Xaa Ala Tyr Asp Xaa Ala Ala
            35                  40                  45

Leu Xaa Phe Lys Gly Xaa Lys Ala Lys Leu Asn Phe Pro
        50                  55                  60

<210> SEQ ID NO 6
<211> LENGTH: 9
<212> TYPE: PRT
<213> ORGANISM: Arabidiopsis thaliana
<220> FEATURE:
<221> NAME/KEY: DOMAIN
<222> LOCATION: (1)...(9)
<223> OTHER INFORMATION: polyglycine domain

<400> SEQUENCE: 6

Gly Gly Gly Tyr Gly Ser Gly Thr Gly
1               5

<210> SEQ ID NO 7
<211> LENGTH: 8
<212> TYPE: PRT
<213> ORGANISM: Arabidiopsis thaliana
<220> FEATURE:
<221> NAME/KEY: DOMAIN
<222> LOCATION: (1)...(8)
<223> OTHER INFORMATION: polyserine domain

<400> SEQUENCE: 7

Ser Ser Ser Ser Gly Gly Ser Ser
1               5

<210> SEQ ID NO 8
<211> LENGTH: 7
<212> TYPE: PRT
<213> ORGANISM: Arabidiopsis thaliana
<220> FEATURE:
<221> NAME/KEY: DOMAIN
<222> LOCATION: (1)...(7)
<223> OTHER INFORMATION: polyserine domain

<400> SEQUENCE: 8
```

```
Ser Ser Ser Ser Pro His Ser
 1               5

<210> SEQ ID NO 9
<211> LENGTH: 4
<212> TYPE: PRT
<213> ORGANISM: Glycine max
<220> FEATURE:
<221> NAME/KEY: DOMAIN
<222> LOCATION: (1)...(4)
<223> OTHER INFORMATION: polyserine domain

<400> SEQUENCE: 9

Ser Ser Ser Ser
 1

<210> SEQ ID NO 10
<211> LENGTH: 5
<212> TYPE: PRT
<213> ORGANISM: Glycine max
<220> FEATURE:
<221> NAME/KEY: DOMAIN
<222> LOCATION: (1)...(5)
<223> OTHER INFORMATION: polyserine domain

<400> SEQUENCE: 10

Ser Ser Leu Ser Ser
 1               5

<210> SEQ ID NO 11
<211> LENGTH: 7
<212> TYPE: PRT
<213> ORGANISM: Glycine max
<220> FEATURE:
<221> NAME/KEY: DOMAIN
<222> LOCATION: (1)...(7)
<223> OTHER INFORMATION: polyserine domain

<400> SEQUENCE: 11

Ser Ser Tyr Ser Ser Ser Ser
 1               5

<210> SEQ ID NO 12
<211> LENGTH: 269
<212> TYPE: PRT
<213> ORGANISM: Oryza sativa

<400> SEQUENCE: 12

Met Val Thr Ala Leu Ala His Val Ile Arg Ala Pro Asp Leu His
 1               5                  10                  15

Leu Pro His His Pro Ser Ser Ser Ala Ser Ala Ala His Pro Gln
                20                  25                  30

Gln Ala Ser Ser Phe Tyr Pro Thr Ala Ala Ala Ala Ser Ser Pro
                35                  40                  45

Ser Asp Gln Leu Ala Ala Ala Ala Ala Ala Glu Glu Gln Gly Arg
        50                  55                  60

Arg Arg His Tyr Arg Gly Val Arg Gln Arg Pro Trp Gly Lys Trp Ala
65                  70                  75                  80

Ala Glu Ile Arg Asp Pro Lys Lys Ala Ala Arg Val Trp Leu Gly Thr
                    85                  90                  95

Phe Asp Thr Ala Glu Asp Ala Ala Ile Ala Tyr Asp Glu Ala Ala Leu
                    100                 105                 110

Arg Phe Lys Gly Thr Lys Ala Lys Leu Asn Phe Pro Glu Arg Val Gln
```

```
            115                 120                 125
Gly Arg Thr Asp Leu Gly Phe Leu Val Thr Arg Gly Ile Pro Pro Ala
    130                 135                 140

Ala Thr His Gly Gly Gly Tyr Tyr Pro Ser Ser Ser Pro Ala Ala Gly
145                 150                 155                 160

Ala Cys Pro Pro Arg Gln Gln Gln Thr Val Val Pro Tyr Pro Asp
                165                 170                 175

Leu Met Arg Tyr Ala Gln Leu Leu Gln Gly Gly Val Gly Gly Ser Tyr
                180                 185                 190

Met Pro Phe Gly Gly Ala Ala Thr Met Ser Ser Ser Thr Val Ser Ser
            195                 200                 205

Ser Ser Ala Pro Gln Ile Leu Asp Phe Ser Thr Gln Gln Leu Ile Arg
    210                 215                 220

Ala Gly Pro Pro Ser Pro Met Pro Ser Ser Gly Ser Ser Ala Thr
225                 230                 235                 240

Ala Ala Ala Ser Ser Thr Thr Ser Ala Ser Ser Pro Gly Ala Trp Pro
                245                 250                 255

Tyr Gly Gly Ser Glu Arg Lys Lys Lys Asp Ser Ser Ser
            260                 265

<210> SEQ ID NO 13
<211> LENGTH: 212
<212> TYPE: PRT
<213> ORGANISM: Arabidopsis thaliana

<400> SEQUENCE: 13

Met Val Ser Ala Leu Ser Arg Val Ile Glu Asn Pro Thr Asp Pro Pro
  1               5                  10                  15

Val Lys Gln Glu Leu Asp Lys Ser Asp Gln His Gln Pro Asp Gln Asp
                20                  25                  30

Gln Pro Arg Arg His Tyr Arg Gly Val Arg Gln Arg Pro Trp Gly
            35                  40                  45

Lys Trp Ala Ala Glu Ile Arg Asp Pro Lys Lys Ala Ala Arg Val Trp
 50                  55                  60

Leu Gly Thr Phe Glu Thr Ala Glu Glu Ala Ala Leu Ala Tyr Asp Arg
65                  70                  75                  80

Ala Ala Leu Lys Phe Lys Gly Thr Lys Ala Lys Leu Asn Phe Pro Glu
                85                  90                  95

Arg Val Gln Gly Pro Thr Thr Thr Thr Ile Ser His Ala Pro Arg
                100                 105                 110

Gly Val Ser Glu Ser Met Asn Ser Pro Pro Arg Pro Gly Pro Pro
            115                 120                 125

Ser Thr Thr Thr Ser Trp Pro Met Thr Tyr Asn Gln Asp Ile Leu
    130                 135                 140

Gln Tyr Ala Gln Leu Leu Thr Ser Asn Asn Glu Val Asp Leu Ser Tyr
145                 150                 155                 160

Tyr Thr Ser Thr Leu Phe Ser Gln Pro Phe Ser Thr Pro Ser Ser Ser
                165                 170                 175

Ser Ser Ser Ser Gln Gln Thr Gln Gln Gln Leu Gln Gln Gln
            180                 185                 190

Gln Gln Arg Glu Glu Glu Lys Asn Tyr Gly Tyr Asn Tyr Asn
        195                 200                 205

Tyr Pro Arg Glu
    210
```

<210> SEQ ID NO 14
<211> LENGTH: 248
<212> TYPE: PRT
<213> ORGANISM: Zea mays

<400> SEQUENCE: 14

Met Glu Ala Ser Asn Glu Ser Ala Pro Thr Ala Glu Ala Ala
1               5                   10                  15

Gly Ser Gly Pro Ala Gly Gly Glu Gly Arg Lys Gly Lys Ala Pro Lys
            20                  25                  30

Gly Gly Pro Glu Asn Gly Lys Phe Arg Tyr Arg Gly Val Arg Gln Arg
        35                  40                  45

Ser Trp Gly Lys Trp Val Ala Glu Ile Arg Glu Pro Arg Lys Arg Ser
    50                  55                  60

Arg Lys Trp Leu Gly Thr Phe Ala Thr Ala Glu Asp Ala Ala Arg Ala
65                  70                  75                  80

Tyr Asp Arg Ala Ala Leu Leu Leu Tyr Gly Pro Arg Ala His Leu Asn
                85                  90                  95

Leu Thr Ser Pro Pro Pro Thr Leu Ala Ala Pro Arg Ser His Pro
            100                 105                 110

His Ser Ser Ala Thr Ser Ser Ala Pro Pro Ala Leu Arg Pro Leu Leu
            115                 120                 125

Pro Arg Pro Pro Leu His Gln Leu Ser Ser Asp Gly Ala Pro Ala Pro
    130                 135                 140

Asp Phe His Tyr His Asn Gln Phe Gln Arg Arg Leu Leu Pro Gln Pro
145                 150                 155                 160

Thr Pro Thr Leu Tyr Tyr Ala Asn Thr Ala Thr Ala Ser Thr Val Thr
                165                 170                 175

Thr Ser Val Pro Thr Arg Val Ala Val Pro Gln Glu Pro Ala Ile Ala
            180                 185                 190

Pro Ala Val Gly Ser Ser Thr Ser Leu Gln Glu Pro Gln Val Gly Thr
        195                 200                 205

Pro Glu Glu Ala Arg Gly Glu Ala Gly Trp Asp Tyr Asn Gly Gly Glu
    210                 215                 220

Glu Glu Asp Tyr Ala Ala Ala Leu Leu Trp Asp Glu Pro Glu Pro Phe
225                 230                 235                 240

Phe Trp Phe Asp Val Phe Leu Lys
                245

<210> SEQ ID NO 15
<211> LENGTH: 328
<212> TYPE: PRT
<213> ORGANISM: Antirrhinum majus

<400> SEQUENCE: 15

Met Asp Pro Leu Ala Ser Gln His Gln His Asn His Leu Glu Asp Asn
1               5                   10                  15

Asn Gln Thr Leu Thr His Asn Asn Pro Gln Ser Asp Ser Thr Thr Asp
            20                  25                  30

Ser Ser Thr Ser Ser Ala Gln Arg Lys Arg Lys Gly Lys Gly Gly Pro
        35                  40                  45

Asp Asn Ser Lys Phe Arg Tyr Arg Gly Val Arg Gln Arg Ser Trp Gly
    50                  55                  60

Lys Trp Val Ala Glu Ile Arg Glu Pro Arg Lys Arg Thr Arg Lys Trp
65                  70                  75                  80

```
Leu Gly Thr Phe Ala Thr Ala Glu Asp Ala Ala Arg Ala Tyr Asp Arg
                85                  90                  95
Ala Ala Val Tyr Leu Tyr Gly Ser Arg Ala Gln Leu Asn Leu Thr Pro
            100                 105                 110
Ser Ser Pro Ser Ser Val Ser Ser Ser Ser Ser Val Ser Ala Ala
        115                 120                 125
Ser Ser Pro Ser Thr Ser Ser Ser Thr Gln Thr Leu Arg Pro Leu
    130                 135                 140
Leu Pro Arg Pro Ala Ala Ala Thr Val Gly Gly Ala Asn Phe Gly
145                 150                 155                 160
Pro Tyr Gly Ile Pro Phe Asn Asn Asn Ile Phe Leu Asn Gly Gly Thr
                165                 170                 175
Ser Met Leu Cys Pro Ser Tyr Gly Phe Phe Pro Gln Gln Gln Gln
            180                 185                 190
Gln Asn Gln Met Val Gln Met Gly Gln Phe Gln His Gln Gln Tyr Gln
            195                 200                 205
Asn Leu His Ser Asn Thr Asn Asn Lys Ile Ser Asp Ile Glu Leu
    210                 215                 220
Thr Asp Val Pro Val Thr Asn Ser Thr Ser Phe His His Glu Val Ala
225                 230                 235                 240
Leu Gly Gln Glu Gln Gly Ser Gly Cys Asn Asn Asn Ser Ser Met
            245                 250                 255
Glu Asp Leu Asn Ser Leu Ala Gly Ser Val Gly Ser Ser Leu Ser Ile
            260                 265                 270
Thr His Pro Pro Pro Leu Val Asp Pro Val Cys Ser Met Gly Leu Asp
        275                 280                 285
Pro Gly Tyr Met Val Gly Asp Gly Ser Ser Thr Ile Trp Pro Phe Gly
        290                 295                 300
Gly Glu Glu Glu Tyr Ser His Asn Trp Gly Ser Ile Trp Asp Phe Ile
305                 310                 315                 320
Asp Pro Ile Leu Gly Glu Phe Tyr
                325

<210> SEQ ID NO 16
<211> LENGTH: 61
<212> TYPE: PRT
<213> ORGANISM: Artificial Sequence
<220> FEATURE:
<223> OTHER INFORMATION: consensus AP2 conserved region
<221> NAME/KEY: VARIANT
<222> LOCATION: 32, 36, 39, 43, 47, 51
<223> OTHER INFORMATION: Xaa = Any Amino Acid
<221> NAME/KEY: VARIANT
<222> LOCATION: 32, 36, 39, 43, 47, 51
<223> OTHER INFORMATION: Xaa = Any Amino Acid
<221> NAME/KEY: VARIANT
<222> LOCATION: 32, 36, 39, 43, 47, 51
<223> OTHER INFORMATION: Xaa = Any Amino Acid

<400> SEQUENCE: 16

His Tyr Arg Gly Val Arg Gln Arg Pro Trp Gly Lys Trp Ala Ala Glu
  1               5                  10                  15
Ile Arg Asp Pro Lys Lys Ala Ala Arg Val Trp Leu Gly Thr Phe Xaa
                20                  25                  30
Thr Ala Glu Xaa Ala Ala Xaa Ala Tyr Asp Xaa Ala Ala Leu Xaa Phe
            35                  40                  45
Lys Gly Xaa Lys Ala Lys Leu Asn Phe Pro Glu Arg Val
    50                  55                  60
```